(12) United States Patent
Inazawa et al.

(10) Patent No.: US 8,183,223 B2
(45) Date of Patent: May 22, 2012

(54) METHOD FOR DETECTING CARCINOMA AND AGENT FOR SUPPRESSING CARCINOMA

(75) Inventors: Johji Inazawa, Tokyo (JP); Ken-ichi Kozaki, Tokyo (JP); Issei Imoto, Tokyo (JP)

(73) Assignees: Fujifilm Corporation, Tokyo (JP); National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 12/964,464

(22) Filed: Dec. 9, 2010

(65) Prior Publication Data
US 2011/0076768 A1 Mar. 31, 2011

Related U.S. Application Data

(62) Division of application No. 12/357,894, filed on Jan. 22, 2009, now abandoned.

(30) Foreign Application Priority Data

Jan. 23, 2008 (JP) ................................. 2008-012256

(51) Int. Cl.
*A61K 48/00* (2006.01)
*C07H 21/04* (2006.01)
*C12Q 1/68* (2006.01)

(52) U.S. Cl. .................. 514/44 A; 536/23.1; 536/24.5; 435/6.1

(58) Field of Classification Search .................. None
See application file for complete search history.

(56) References Cited

FOREIGN PATENT DOCUMENTS

| WO | WO-2005/078139 A2 | 8/2005 |
| WO | WO-2006/137941 A2 | 12/2006 |
| WO | WO-2007/081720 A2 | 7/2007 |

OTHER PUBLICATIONS

Kozaki et al., Apr. 1, 2008, Cancer Research, vol. 68, pp. 2094-2105.*
Tran et al., "MicroRNA expression profiles in head and neck cancer cell lines", Biochemical and Biophysical Research Communications, vol. 358, No. 1, pp. 12-17, Jun. 22, 2007, Published by Elsevier Inc. (XP002532710).
Sun et al., "Development of a micro-array to detect human and mouse microRNAs and characterization of expression in human organs", Nucleic Acids Research, vol. 32, No. 22, p. e188, 2004, Published by Oxford University Press. (XP002532711).
Thomson et al., "A custom microarray platform for analysis of microRNA gene expression", Nature Methods, vol. 1, No. 1, pp. 47-53, Oct. 2004. (XP002532712).
Barad et al., "MicroRNA expression detected by oligonucleotide microarrays: System establishment and expression profiling in human tissues", Genome Research, vol. 14, No. 12, pp. 2486-2494, Dec. 2004, Published by Cold Spring Harbor Laboratory Press. (XP002532713).
Perera, "A Microarray-based method to profile global microRNA expression in human and mouse", in *Methods in Molecular Biology*, pp. 137-148, Jan. 2007, Published by Humana Press Inc., Totowa, NJ (XP009104056).
Ha et al., "Promoter methylation and inactivation of tumour-suppressor genes in oral squamous-cell carcinoma", The Lancet Oncology, vol. 7, No. 1, pp. 77-82, Jan. 2006. (XP002532714).
Hebert et al., "High mobility group A2 is a target for miRNA-98 in head and neck squamous cell carcinoma", Molecular Cancer, vol. 6:5, Jan. 2007. (XP002532715).
Xiong et al., "COBRA: a sensitive and quantitative DNA methylation assay", Nucleic Acids Research, vol. 25, No. 12, pp. 2532-2534, Jun. 1997. (XP002532716).
USPTO Non-Final Office Action, U.S. Appl. No. 12/357,894, Sep. 9, 2010, pp. 1-8.

* cited by examiner

*Primary Examiner* — Dana Shin
(74) *Attorney, Agent, or Firm* — Birch, Stewart, Kolasch & Birch, LLP

(57) ABSTRACT

The present invention is directed to methods for suppressing the growth of oral squamous-cell carcinoma cells. The methods include introducing at least one gene selected from miR-137 or miR-193a into oral squamous-cell carcinoma cells.

3 Claims, 17 Drawing Sheets

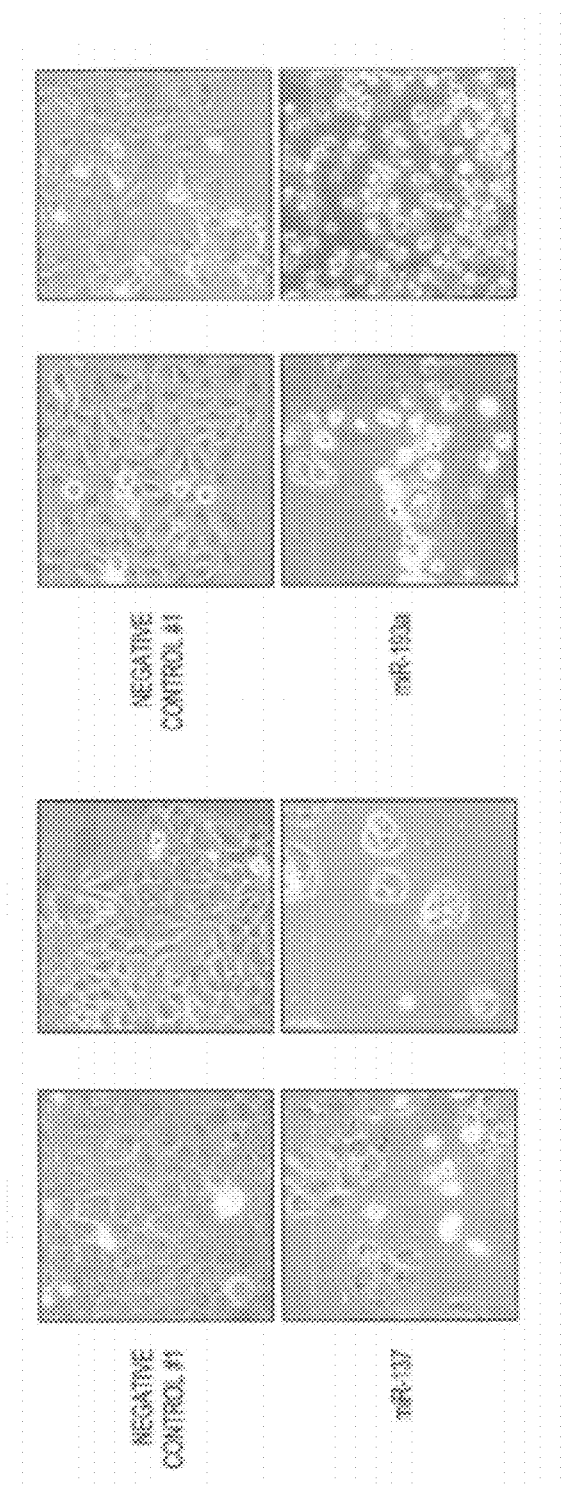
FIG.4A (CONTD)

SEQUENCE LISTING

```
<160> NUMBER OF SEQ ID NOS: 26

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
ggagtggagg agttttttgt t                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
aaataccaaa cctcccttc                                                 20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
ttagttttag ggtttggggt t                                              21

<210> SEQ ID NO 4
<211> LENGTH: 24
<212> TYPE: DNA
<213> ORGANISM: Artificial Sequence
<220> FEATURE:
```

<223> OTHER INFORMATION: Description of Artificial Sequence: Synthetic
      DNA

<400> SEQUENCE: 4
ttataaccac cacaatacaa tcaa                                          24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
ttttggtttt agattgttta ttg                                           23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
aaactattac ctccaattcc c                                             21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
gtttyggaaa gttaattttt tg                                            22

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
cctcactttc ctaaaaaaat aac                                           23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
gttatttttt taggaaagtg agg                                           23

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA -continued

<400> SEQUENCE: 10
actctactac tccrcctcc                                                    19

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
ttttggtttt agattgttta ttg                                               23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
aaactattac ctccaattcc c                                                 21

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
tttttttgtg ttaagtattt gattt                                             25

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
aaaaaaatac taccttaaca acca                                              24

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
aaagggaaaa ttattgggtt t                                                 21

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
aacccctcra actcctaa                                         18

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17 ttttaattt ygagggtt                                          19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
caaccctcca aaaattaca                                        19

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
gaggttttgg ttttygtatt t                                     21

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
ccttctccaa crtaaacct                                        19

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
ttagatttgg ggtaagtgtt ga                                    22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
ccctctcact tcaaaaaaaa ct                                    22

```
<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23 agttttttt gaagtgagag gg                                           22

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24 cacccctac cctactacaa                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
gttgtagtag ggtagggggt                                             20

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
acccctaact ataactctaa ctcca                                       25
```

METHOD FOR DETECTING CARCINOMA AND AGENT FOR SUPPRESSING CARCINOMA

This is a Division of U.S. application Ser. No. 12/357,894 filed on Jan. 22, 2009 now abandoned. U.S. application Ser. No. 12/357,894 claims the benefit of priority of Japanese Application No. 2008-012256 filed on Jan. 23, 2008 under 35 U.S.C. §119. The entire contents of all of the aforementioned applications are incorporated herein by reference.

TECHNICAL FIELD

The present invention relates to a method of detecting carcinomas, such as oral squamous-cell carcinoma by utilizing changes in the expression levels of microRNA genes that are present in the human chromosome, and more particularly to an agent for suppressing growth of carcinoma, such as oral squamous-cell carcinoma.

BACKGROUND ART

Oral squamous-cell carcinoma (OSCC) is classified as a head and neck carcinoma and is a tumor that is mainly generated from oral mucous membrane epithelia and the like. Among head and neck carcinomas, OSCC incidence is as high as about 35% and it is assumed to develop in about 270,000 people worldwide every year (Parkin, D. M., et al., CA Cancer J Clin. 55, 74-108, 2002). In Japan, 5,500 or more people had died thereof in 2003. The most common site of the origin of oral squamous-cell carcinoma is tongue and the second most common site thereof is gingiva (gum). Oral squamous-cell carcinoma is known to be developed at other mucous membranes of the oral cavity such as buccal mucosa, palate, and mouth floor. Furthermore, oral squamous-cell carcinoma is also known to be developed at jawbone or salivary gland.

In recent years, although methods for diagnosis and treatment for oral squamous-cell carcinoma have been advanced, the prognosis thereof has remained unimproved. Accordingly, it has been necessary to discover a causative gene for oral squamous-cell carcinoma and changes that have occurred in such gene to elucidate the functions for establishment of new therapeutic strategy for development of more effective therapeutic methods and chemical prevention.

DISCLOSURE OF THE INVENTION

Successful elucidation of the mechanism of malignant transformation of oral-cavity-derived cells and mainly oral mucous membrane epithelium-derived cells at the gene level will enable detection of malignant transformation of oral mucous membrane epithelium cells at the gene level, diagnosis of the malignancy of oral squamous-cell carcinoma, and suppression of the advancement thereof Furthermore, it will also enable establishment of methods for selecting and developing drugs and methods for therapy, based on such mechanisms. Specifically, identifying genes exhibiting characteristic behavior observed in oral squamous-cell carcinoma cases and then carrying out technical examination mainly targeting such genes can achieve this object. Hence, an object to be achieved by the present invention is to identify genes exhibiting characteristic behavior in the cases of carcinoma such as oral squamous-cell carcinoma, so as to provide a method for detecting carcinoma and an agent for suppressing carcinoma.

The real-time reverse transcription-polymerase chain reaction (Real-time RT-PCR) is the best method for conveniently and rapidly analyzing the amount of transcripts resulting from gene expression. In order to analyze changes in expression of genes associated with carcinoma, TaqMan MicroRNA Assays was used, and the carcinoma-associated microRNA genes, which would accelerate malignant transformation of oral mucous membrane epithelium cells, shown in Tables 1 and 2 were successfully identified. The expression levels of miR-34b, miR-132, miR-137, miR-193a, and miR-203 located on or around the CpG islands are down-regulated also by methylation of cytosine that is present on CpG islands. Specifically, down-regulated expression levels of such genes result in acceleration of oral squamous-cell carcinoma growth. Further, the present inventors discovered that the up-regulated expression levels of such genes in oral squamous-cell carcinoma would significantly down-regulate carcinoma growth. This has led to the completion of the present invention.

The present invention provides a method for detecting carcinoma, which comprises detecting malignant transformation of specimens by employing an up-regulated expression level of at least one gene selected from the group consisting of miR-374, miR-340, miR-224, miR-10a, miR-140, miR-213, miR-146a, miR-126, miR-31, miR-9, and miR-9*, and/or a down-regulated expression level of at least one gene selected from the group consisting of miR-27a, miR-34b, miR-34c, miR-203, miR-302c*, miR-23a, miR-27b, miR-34a, miR-215, miR-299, miR-330, miR-337, miR-107, miR-133b, miR-138, miR-139, miR-223, miR-204, miR-370, let-7d, miR-95, miR-302a, miR-367, let-7g, miR-23b, miR-128a, miR-148a, miR-155, miR-200c, miR-302b, miR-368, miR-122a, miR-371, let-7a, miR-26b, miR-30e-5p, miR-96, miR-125a, miR-132, miR-200b, miR-199b, miR-296, miR-373*, miR-137, miR-197, miR-193a, let-7e, miR-30d, miR-331, miR-342, miR-338, miR-199a, miR-372, and miR-184 as indicators.

Preferably, changes in gene expression are detected by using the DNA array method, Northern blotting, RT-PCR, real-time RT-PCR, RT-LAMP, or in situ hybridization.

Preferably, the down-regulated gene expression level results from methylation of CpG islands or in the vicinity thereof.

Preferably, the methylation is detected by using the COBRA method, bisulfite sequencing, or Southern blotting.

Preferably, the down-regulated expression level of at least one gene selected from among miR-34b, miR-132, miR-137, miR-193a, and miR-203 is employed as an indicator to detect malignant transformation of specimens.

Preferably, the specimen is an oral-cavity-derived cell.

Preferably, the carcinoma is oral squamous-cell carcinoma.

According to another aspect, the present invention provides an agent for suppressing carcinoma, which comprises at least one gene selected from the group consisting of miR-27a, miR-34b, miR-34c, miR-203, miR-302c*, miR-23a, miR-27b, miR-34a, miR-215, miR-299, miR-330, miR-337, miR-107, miR-133b, miR-138, miR-139, miR-223, miR-204, miR-370, let-7d, miR-95, miR-302a, miR-367, let-7g, miR-23b, miR-128a, miR-148a, miR-155, miR-200c, miR-302b, miR-368, miR-122a, miR-371, let-7a, miR-26b, miR-30e-5p, miR-96, miR-125a, miR-132, miR-200b, miR-199b, miR-296, miR-373*, miR-137, miR-197, miR-193a, let-7e, miR-30d, miR-331, miR-342, miR-338, miR-199a, miR-372, and miR-184.

Preferably, the agent for suppressing carcinoma according to the present invention comprises at least one of miR-34b, miR-132, miR-137, miR-193a, and miR-203 genes.

Preferably, the gene is bound to or incorporated in a polymer compound.

Preferably, the polymer compound is a liposome.

Preferably, the carcinoma is oral squamous-cell carcinoma.

The present invention enables accurate understanding of malignant transformation in cell specimens derived from the oral mucosa. Also, introduction of synthetic double-stranded RNA containing the microRNA sequence into the oral squamous-cell carcinoma would be able to suppress the growth of carcinoma, such as oral squamous-cell carcinoma.

BEST MODES FOR CARRYING OUT THE PRESENT INVENTION

Figure 1A:
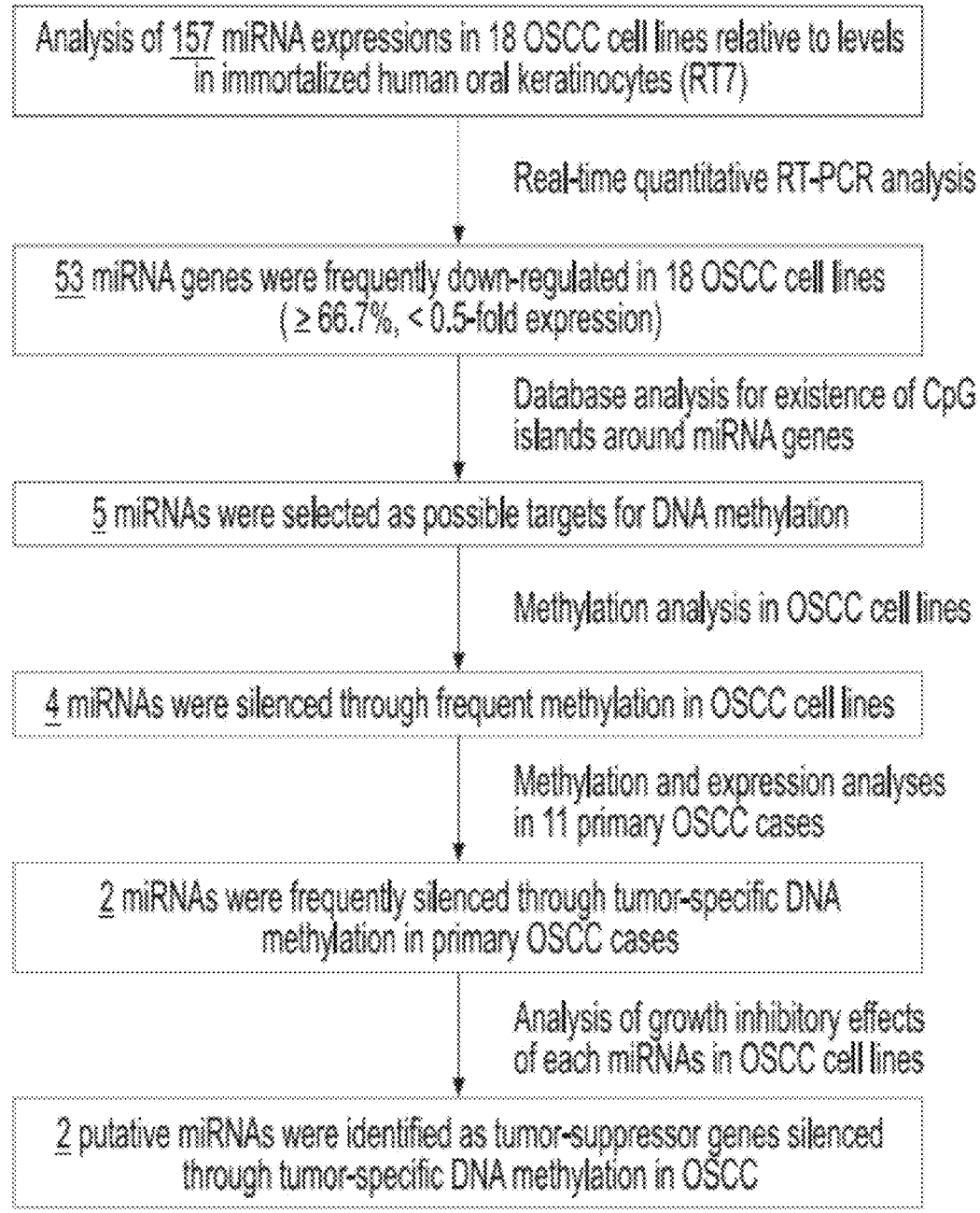
FIG. 1 shows the strategy of the study and the results of miRNA expression analysis in the oral squamous-cell carcinoma cells. FIG. A shows a strategy for isolating antioncogenic miRNA, the expression of which is epigenetically suppressed in the oral squamous-cell carcinoma cells. FIG. B shows expression profiles of 157 types of miRNA genes in 18 types of oral squamous-cell carcinoma cells and in the RT7 cells obtained with the use of the TaqMan Micro RNA Assays Human Panel Early Access Kit; and U represents miRNA, the expression of which was not observed in the RT7 cells. The miRNA expression levels were compared in terms of relative value based on the RNU6B expression level as an internal control. Stars represent 21 types of miRNA genes located on or around the CpG islands. FIG. C shows expression levels of candidate miRNA genes located on or around the CpG islands in 18 types of oral squamous-cell carcinoma cells. A bar graph representing each cell line represents a comparison of expression levels in the RT7 cells and in each cell line. Asterisks (*) represent a frequency of oral squamous-cell carcinoma cell lines in which down-regulated expression levels (expression levels of less than 0.5-fold) of candidate miRNA, compared with the RT7 cells, had been observed. FIG. D shows recovery of candidate miRNA gene expression after treatment with 10 μM 5-aza-dCyd. A bar graph representing each cell line indicates a comparison of expression levels in untreated cells and in treated cells. Stars represent cell lines in which significantly down-regulated gene expression was not observed via TaqMan real-time RT-PCR analysis (FIG. 1C). Asterisks (*) represent a frequency of oral squamous-cell carcinoma cell lines in which recovery of candidate miRNA expression (expression levels of more than 1.5-fold) was observed by comparing untreated cells with cells that have been treated with 10 μM 5-aza-dCyd.

Hereafter, the present invention is described in greater detail.

(1) Method for Detecting Cancer

The method for detecting carcinoma according to the present invention comprises detecting malignant transformation of specimens using at least one of changes in expression of genes shown in Table 1 and Table 2 as indicators. The term "changes in expression of genes" used herein refers to up-regulation or down-regulation of gene expression. Particularly preferably, down-regulated expression levels of microRNA (miRNA) genes (i.e., miR-34b, miR-132, miR-137, miR-193a, or miR-203) in specimens can be detected to identify malignant transformation of specimens. Particularly preferably, down-regulated expression levels of miR-34b, miR-132, miR-137, miR-193a, and miR-203 genes in oral-cavity-derived cells can be detected to identify malignant transformation of oral-cavity-derived cells. Further, miR-34b, miR-132, miR-137, miR-193a, and miR-203 can be bound to or incorporated in polymer compounds, and the resultants can then be introduced into oral squamous-cell carcinoma cells to suppress growth of carcinoma.

As a result of the human genome project etc., transcripts of the miR-34b, miR-132, miR-137, miR-193a, and miR-203 are already known via TaqMan Micro RNA assays, and such transcripts are microRNA genes that are located in chromosomal regions 11q23.1, 17p13.3, 1p21.3, 17q11.2, and 14q32.33. Detailed functions of miR-34b, miR-132, miR-137, miR-193a, and miR-203 genes remain unknown. The fact that such miRNA is an important cancer-associated gene involved in the onset of oral squamous-cell carcinoma was unknown before the present invention.

As described above, the detection method according to a preferable embodiment of the present invention comprises detecting down-regulated expression levels of miR-34b, miR-132, miR-137, miR-193a, and miR-203 genes in oral-mucosa-derived cells or oral squamous-cell carcinoma.

Target oral-mucosa-derived cells or oral squamous-cell carcinoma cells in which down-regulated expression levels of miR-34b, miR-132, miR-137, miR-193a, and miR-203 genes are to be detected are preferably biopsy tissue cells obtained from a specimen donor.

Such tissue cell specimen may be an oral-cavity-derived cell of a healthy subject or a cancerous tissue of an oral squamous-cell carcinoma patient. In practice, examples of a major target tissue specimen that can be used herein include: a tissue obtained from a lesion in which suspected malignant transformation of the mucous membrane of oral cavity, tongue, gum, or the like is observed by a test or the like; and an oral squamous-cell carcinoma tissue that has been confirmed to be derived from oral squamous-cell carcinoma and thus must be subjected to determination of malignancy or the stage progression of oral squamous-cell carcinoma.

In a case in which down-regulated expression levels of miR-34b, miR-132, miR-137, miR-193a, and miR-203 genes are observed in "a tissue obtained from a lesion in which suspected malignant transformation of oral-cavity-derived tissues or cells is observed in a test or the like" by the detection method of the present invention, it is understood that such lesion tissue will reach (or has reached) the state of malignant transformation so that the level of malignancy of the disease will increase. Thus, there is a demonstrated urgent need for implementation of a full-scale therapy (e.g., elimination of a lesion via a surgery or the like and full-scale chemotherapy).

In addition, in a case in which the down-regulated expression levels of miR-34b, miR-132, miR-137, miR-193a, and miR-203 genes are observed in "an oral squamous-cell carcinoma tissue that has been confirmed to be derived from oral squamous-cell carcinoma and thus must be subjected to determination of malignancy or the stage progression of oral squamous-cell carcinoma," it is also understood that the level of malignancy of the cancerous tissue will increase. Thus, there is a demonstrated urgent need for implementation of full-scale therapy (e.g., elimination of a lesion via a surgery or the like and full-scale chemotherapy). An oral squamous-cell carcinoma tissue collected as a specimen may be subjected to necessary treatment such as preparation of DNA or RNA from the collected tissue followed by the detection method of the present invention.

The sequence information regarding microRNA shown in Tables 1 and 2 used in the present invention has been registered in the Wellcome Trust Sanger Institute miRBase (microrna.sanger.ac.uk/). The accession numbers thereof are shown below.

| miRNA | miRBase Accessions |
|---|---|
| miR-374 | MIMAT0000727 |
| miR-340 | MIMAT0004692 |
| miR-224 | MIMAT0000281 |
| miR-10a | MIMAT0000253 |
| miR-140 | MIMAT0000431 |
| miR-213 | MIMAT0000256 |
| miR-146a | MIMAT0000449 |
| miR-126 | MIMAT0000445 |
| miR-31 | MIMAT0000089 |
| miR-9 | MIMAT0000441 |
| miR-9* | MIMAT0000442 |
| miR-27a | MIMAT0000084 |
| miR-34b | MIMAT0004676 |
| miR-34c | MIMAT0000686 |
| miR-203 | MIMAT0000264 |
| miR-302c* | MIMAT0000716 |
| miR-23a | MIMAT0000078 |
| miR-27b | MIMAT0000419 |
| miR-34a | MIMAT0000255 |
| miR-215 | MIMAT0000272 |
| miR-299 | MIMAT0002890 |
| miR-330 | MIMAT0004693 |
| miR-337 | MIMAT0004695 |
| miR-107 | MIMAT0000104 |
| miR-133b | MIMAT0000770 |
| miR-138 | MIMAT0000430 |
| miR-139 | MIMAT0000250 |
| miR-223 | MIMAT0000280 |
| miR-204 | MIMAT0000265 |
| miR-370 | MIMAT0000722 |
| let-7d | MIMAT0000065 |
| miR-95 | MIMAT0000094 |
| miR-302a | MIMAT0000684 |
| miR-367 | MIMAT0000684 |
| let-7g | MIMAT0000414 |
| miR-23b | MIMAT0000078 |
| miR-128a | MIMAT0000424 |
| miR-148a | MIMAT0000243 |
| miR-155 | MIMAT0000646 |
| miR-200c | MIMAT0000617 |
| miR-302b | MIMAT0000715 |
| miR-368 | MIMAT0000720 |
| miR-122a | MIMAT0000421 |
| miR-371 | MIMAT0004687 |
| let-7a | MIMAT0000062 |
| miR-26b | MIMAT0000083 |
| miR-30e-5p | MIMAT0000692 |

-continued

| miRNA | miRBase Accessions |
|---|---|
| miR-96 | MIMAT0000095 |
| miR-125a | MIMAT0000443 |
| miR-132 | MIMAT0000426 |
| miR-200b | MIMAT0000318 |
| miR-199b | MIMAT0000263 |
| miR-296 | MIMAT0000690 |
| miR-373* | MIMAT0000725 |
| miR-137 | MIMAT0000429 |
| miR-197 | MIMAT0000227 |
| miR-193a | MIMAT0004614 |
| let-7e | MIMAT0000066 |
| miR-30d | MIMAT0000245 |
| miR-331 | MIMAT0004700 |
| miR-342 | MIMAT0004694 |
| miR-338 | MIMAT0004701 |
| miR-199a | MIMAT0000231 |
| miR-372 | MIMAT0000724 |
| miR-184 | MIMAT0000454 |

(2) Changes in miRNA Gene Expression in Oral Squamous-Cell Carcinoma

An example of a representative method that can directly detect changes in miRNA gene expression levels is real-time RT-PCR.

The method for detecting mature miRNA is preferably and practically carried out using TaqMan Micro RNA Assays (Applied Biosystems). Detection may be carried out via Northern blot analysis or the like, although TaqMan Micro RNA Assays is more convenient and sensitive.

(3) Detection of Down-Regulated Expression of miRNA Gene in Oral Squamous-Cell Carcinoma It has been reported that transcriptional inactivation occurs when a CpG-rich promoter region and an exon region are densely methylated (Bird AP., et al., Cell, 99, 451-454, 1999). In the cases of carcinoma cells, CpG islands are frequently and densely methylated compared with other regions, and thus hypermethylation of a promoter region is deeply involved in the inactivation of an antioncogene of a carcinoma (Ehrlich M., et al, Oncogene, 21, 6694-6702, 2002). As described below, CpG islands actually exist in the vicinity of the miR-34b, miR-132, miR-137, miR-193a, and miR-203 genes. In addition, the extent of methylation of the CpG islands was strongly correlated with suppression of the expression of the miR-34b, miR-132, miR-137, miR-193a, and miR-203 genes in some oral squamous-cell carcinoma cases. In addition, it was possible to demethylate such CpG islands by culturing such oral squamous-cell carcinoma cells in the presence of 5-aza-2'-deoxycytidine (5-aza-dCyd) serving as a demethylating reagent. As a result, it was possible to recover the expression levels of the miR-34b, miR-132, miR-137, miR-193a, and miR-203 genes. Based on the above results, it has been revealed that hypermethylation of CpG islands is a cause of frequently occurring suppression of the expression of antioncogenic miRNA genes in squamous-cell carcinoma.

(4) Method for Suppressing Carcinoma, and Agent for Suppressing Carcinoma

The present invention further provides a method for suppressing carcinoma which comprises introducing miRNA, which is a transcript of the miRNA gene (particularly preferably the miR-34b, miR-132, miR-137, miR-193a, or miR-203 gene), into cells, which are listed in Tables 1 and 2 as genes, the expression levels of which are down-regulated in OSCC cells, and an agent for suppressing the carcinoma which comprises the above gene.

The term "miRNA" refers to 10-bp or longer short double-stranded RNA, which is artificially and chemically synthesized, biologically synthesized, synthesized in vivo, or generated via degradation of double-stranded RNA having about 40 or more nucleotides in vivo. In general, miRNA has a 5'-phosphoric acid or 3'-OH structure, and the 3' end is protruded by approximately 2 nucleotides.

The agent for suppressing carcinoma of the present invention can be prepared by incorporating the above gene as an active ingredient together with a base which is commonly used for an agent for gene therapy. When the above gene is incorporated into a virus vector, virus particles containing recombinant vectors are prepared, and the resultants are incorporated with a base which is commonly used for an agent for gene therapy.

As a base used for incorporating the gene as an active ingredient, a base that is commonly used for an injection can be used. Examples include distilled water, a salt solution of sodium chloride or a mixture of sodium chloride and an inorganic salt, a solution of mannitol, lactose, dextran, or glucose, an amino acid solution of glycine or arginine, an organic acid solution, and a mixed solution of a salt solution and a glucose solution. Alternatively, an adjuvant, such as a regulator of osmotic pressure, a pH adjuster, vegetable oil, or a surfactant, may be added to the base in accordance with a technique known in the art to prepare an injection in the form of a solution, suspension, or dispersion. Such injection can be prepared in the form of a preparation to-be-dissolved before use via operations, such as pulverization or lyophilization.

The agent for suppressing carcinoma of the present invention may be administered systemically, for example, common intravenous or intraarterial administration. Alternatively, topical administration, such as topical injection or oral administration, may be employed. Further, the agent for suppressing carcinoma can be administered in combination with catheterization, gene introduction, surgery, or the like. Specifically, the agent for suppressing carcinoma of the present invention may be administered orally, parenterally (e.g., intravenous, intramuscular, hypodermic, subcutaneous, mucosal, intrarectal, intravaginal, topical administration to a lesion, or percutaneous administration), or via direct administration to the lesion. When the agent of the present invention is used in the form of a pharmaceutical composition, a pharmaceutically acceptable additive can be mixed according to need. Specific examples of a pharmaceutically acceptable additive include, but are not limited to, an antioxidant, a preservative, a colorant, a flavoring agent, a diluent, an emulsifier, a suspending agent, a solvent, a filler, an augmentor, a buffer, a delivery vehicle, a diluent, a carrier, an excipient, and/or a pharmaceutical adjuvant.

The agent for suppressing carcinoma of the present invention may be used in any form without particular limitation, and examples include, a liquid, an injection, and a controlled-release agent. A solvent used for preparing the agent of the present invention into the above preparation may be aqueous or nonaqueous.

Further, miRNA as an active ingredient of the agent for suppressing carcinoma of the present invention can be administered via, for example, a method of using a liposome to introduce nucleic acid molecules (e.g., the liposome method, the HVJ-liposome method, the cationic liposome method, the lipofection method, or the lipofectamine method), microinjection, or a method of using a gene gun to transfer nucleic acid molecules together with carriers (i.e., metal particles) to the cells. When the agent is administered to a living body with the use of miRNA, a virus vector, such as a recombinant adenovirus or retrovirus vector, can be used. The miRNA gene is incorporated into DNA or RNA viruses, such as detoxicated retrovirus, adenovirus, adeno-associated virus, herpes virus, vaccinia virus, pox virus, poliovirus, Sindbis virus, Sendai virus, or SV40, and the cell or tissue is infected with the recombinant virus to introduce the gene of interest into cells or tissue.

A person skilled in the art can determine the dose of the agent for suppressing carcinoma of the present invention in accordance with the purpose of use, severity of the disease, the age, the body weight, sex, or a history of use of a patient, or a type of miRNA as an active ingredient. The dose of miRNA is not particularly limited. For example, it is approximately 0.1 ng to approximately 100 mg/kg/day, and preferably approximately 1 ng to approximately 10 mg/kg/day. In general, the effects of miRNA appear 1 to 3 days after the administration. Thus, it is preferable that the agent be administered at a frequency of daily to once every three days. When an expression vector is used, administration can be carried out approximately once in a week.

The present invention is hereafter described in greater detail with reference to the following examples, although the present invention is not limited thereto.

EXAMPLES

Example 1

Changes in miRNA Gene Expression in Oral Squamous-Cell Carcinoma

To detect changes in miRNA gene expression in oral squamous-cell carcinoma, 18 types of oral squamous-cell carcinoma cell lines (Ca9-22, HO-1-N-1, HSC-2, HSC-3, HSC-4, KOSC-2 c13-43, HOC-313, HOC-815, HSC-5, HSC-6, HSC-7, KON, NA, OM1, 0M2, SKN3, TSU, and ZA) were used. As a control, a normal oral mucosal epithelium-derived immortalized cell line, RT7, was used. The oral squamous-cell carcinoma cell line was cultured in DMEM medium containing streptomycin (100 μg/ml), penicillin (100 units/ml), 2 mM glutamine, and 10% fetal bovine serum (FBS). The RT7 cell line was cultured using the KGM-2 Bullet Kit (Cambrex). Genomic DNA was extracted therefrom using the Genome DNA Purification kit (Gentra, Minneapolis, Minn.), and RNA was extracted using Isogen (Nippon Gene), in accordance with manufacturers' instructions.

FIG. 1A shows the strategy for isolating antioncogenic miRNA, the gene expression level of which has been down-regulated due to methylation of tumor-specific DNA in oral squamous-cell carcinoma, and partial results thereof.

At the outset, 18 types of oral squamous-cell carcinoma cell lines and control RT7 cells were used to perform expression profiling of 157 types of mature miRNA genes. Such expression profiling based on real-time RT-PCR was carried out using ABI Prism 7500 Fast Real-time PCR (Applied Biosystems), TaqMan Universal PCR Master Mix (Applied Biosystems), the TaqMan Reverse Transcription Kit (Applied Biosystems), TaqMan Micro RNA Assays (Applied Biosystems), and the Human Panel Early Access Kit (Applied Biosystems) in accordance with the manufacturers' instructions.

Among the 157 types of miRNA genes, miR-124b, miR-144, miR-199-s, and miR-104 are not currently available for TaqMan Micro RNA Assays and thus were excluded from the targets of the analysis of the study. In oral squamous-cell carcinoma, expression levels of miR-154, miR-211, miR-220, miR-302c, and miR-323 genes could not be determined This is because such gene expression could not be detected via real-time RT-PCR analysis in the RT7 cells for normalization.

In comparison with expression levels of miRNA genes in the RT7 cells, up-regulation in expression of 11 types of miRNA genes (7.4%) (i.e., expression levels of more than 1.5-fold; more than 66.7% of oral squamous-cell carcinoma cell lines) and down-regulation of expression of 54 types of miRNA genes (36.5%) (i.e., expression levels of less than 0.5-fold; more than 66.7% of oral squamous-cell carcinoma cell lines) were observed (Table 1 and Table 2).

TABLE 1

Frequencies of OSCC cell lines with remarkable differences of miRNA expression from that in RT7 (≧66.7% of OSCC cell lines)

| miRNA | Locus | Frequency (%) |
|---|---|---|
| miRNAs frequently up-regulated in OSCC cell lines (>1.5-fold expression) | | |
| miR-374 | Xq13.2 | 100.00 |
| miR-340 | 5q35.3 | 83.3 |
| miR-224 | Xq26 | 83.3 |
| miR-10a | 17q21.32 | 77.8 |
| miR-140 | 16q22.1 | 77.8 |
| miR-213 | 1q31.3 | 77.8 |
| miR-146a | 5q33.3 | 72.2 |
| miR-126 | 9q34.3 | 66.7 |
| miR-31 | 9p21.3 | 66.7 |
| miR-9 | miR-9-1, 1q22; miR-9-2, 5q14.3; miR-9-3, 15q26.1 | 66.7 |
| miR-9* | miR-9-1, 1q22; miR-9-3, 15q26.1 | 66.7 |
| miRNAs frequently down-regulated in OSCC cell lines (<0.5-fold expression) | | |
| miR-27a | 19p13.12 | 100.00 |
| miR-34b | 11q23.1 | 100.00 |
| miR-34c | 11q23.1 | 100.00 |
| miR-203 | 14q32.33 | 100.00 |
| miR-302c* | 4q25 | 100.00 |
| miR-23a | 19p13.12 | 94.4 |
| miR-27b | 9q22.32 | 94.4 |
| miR-34a | 1p36.23 | 94.4 |
| miR-215 | 1q41 | 94.4 |
| miR-299 | 14q32.31 | 94.4 |
| miR-330 | 19q13.32 | 94.4 |
| miR-337 | 14q32.31 | 94.4 |
| miR-107 | 10q23.31 | 88.9 |
| miR-133b | 6p12.2 | 88.9 |
| miR-138 | miR-138-1, 3p21.33; miR-138-2, 16q13 | 88.9 |
| miR-139 | 11q13.4 | 88.9 |
| miR-223 | Xq12 | 88.9 |
| miR-204 | 9q21.11 | 88.9 |
| miR-370 | 14q32.31 | 88.9 |
| let-7d | 9q22.32 | 83.3 |
| miR-95 | 4p16.1 | 83.3 |

TABLE 2

| miR-302a | 4q25 | 83.3 |
|---|---|---|
| miR-367 | 4q25 | 83.3 |
| let-7g | 3p21.1 | 77.8 |
| miR-23b | 9q22.32 | 77.8 |
| miR-128a | 2q21.3 | 77.8 |
| miR-148a | 7p15.2 | 77.8 |
| miR-155 | 21q21.3 | 77.8 |
| miR-200c | 12p13.31 | 77.8 |
| miR-302b | 4q25 | 77.8 |
| miR-368 | 14q32.31 | 77.8 |
| miR-122a | 18q21.31 | 77.8 |
| miR-371 | 19q13.41 | 77.8 |
| let-7a | let-7a-1, 9q22.32; let-7a-2, 11q24.1; let-7a-3, 22q13.31 | 72.2 |
| miR-26b | 2q35 | 72.2 |
| miR-30e-5p | 1p34.2 | 72.2 |
| miR-96 | 7q32.2 | 72.2 |

TABLE 2-continued

| miR-125a | 19q13.33 | 72.2 |
|---|---|---|
| miR-132 | 17p13.3 | 72.2 |
| miR-200b | 1p36.33 | 72.2 |
| miR-199b | 9q34.11 | 72.2 |
| miR-296 | 20q13.32 | 72.2 |
| miR-373* | 19q13.41 | 72.2 |
| miR-137 | 1p21.3 | 72.2 |
| miR-197 | 1p13.3 | 72.2 |
| miR-193a | 17q11.2 | 72.2 |
| let-7e | 19q13.33 | 66.7 |
| miR-30d | 8q24.22 | 66.7 |
| miR-331 | 12q22 | 66.7 |
| miR-342 | 14q32.2 | 66.7 |
| miR-338 | 17q25.3 | 66.7 |
| miR-199a | miR-199a-1, 19q13.2; miR-199a-2, 1q24.3 | 66.7 |
| miR-372 | 19q13.41 | 66.7 |
| miR-184 | 15q25.1 | 66.7 |

Example 2

Analysis of Candidate miRNA and Methylation in Oral Squamous-Cell Carcinoma Cell Lines The human genome database (genome.ucsc.edu/) was screened for the presence of CpG islands in the vicinities of 157 types of miRNA genes. As a result, 21 types of miRNA genes were found to be located on or around (within 1,000-bp) the CpG islands (Table 3).

TABLE 3

21 miRNAs located on/around CpG islands

| miRNA | Locus |
|---|---|
| miR-9 | miR-9-1, 1q22; miR-9-3, 15q26.1 |
| miR-9* | miR-9-1, 1q22; miR-9-3, 15q26.1 |
| miR-34b | 11q23.1 |
| miR-92 | miR-92-1, 13q31.3; miR-92-2, Xq26.2; miR-92b, 1q22 |
| miR-124a | miR-124a-1, 8p23.1; mir-124a-2, 8q12.3; miR-124a-3, 20q13.33 |
| miR-126 | 9q34.3 |
| miR-127 | 14q32.31 |
| miR-129 | miR-129-1, 7q32.1; miR-129-2, 11p11.2 |
| miR-132 | 17p13.3 |
| miR-137 | 1p21.3 |
| miR-149 | 2q37.3 |
| miR-152 | 17q21.32 |
| miR-189 | 9q22.32 (Replaced by miR-21-1) |
| miR-191 | 3p21.31 |
| miR-193a | 17q11.2 |
| miR-203 | 14q32.33 |

TABLE 3-continued 21 miRNAs located on/around CpG islands

| miRNA | Locus |
|---|---|
| miR-210 | 11p.15.5 |
| miR-219 | miR-219-1, 6p21.32; miR-219-2, 9q34.11 |
| miR-320 | 8p21.3 |
| miR-339 | 7p22.3 |
| let-7i | 12q14.1 |

Figure 1B:
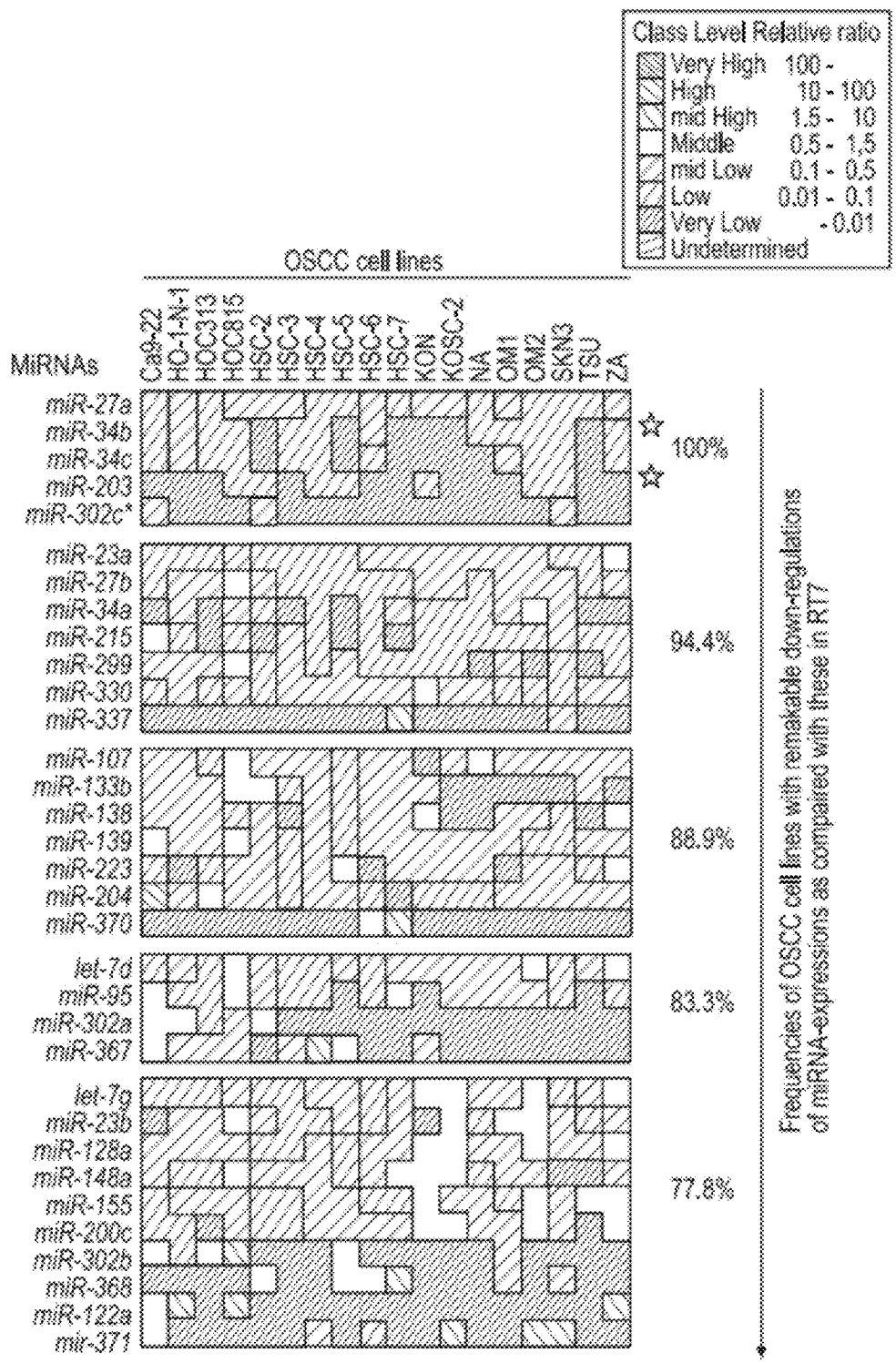
Figure 1B:
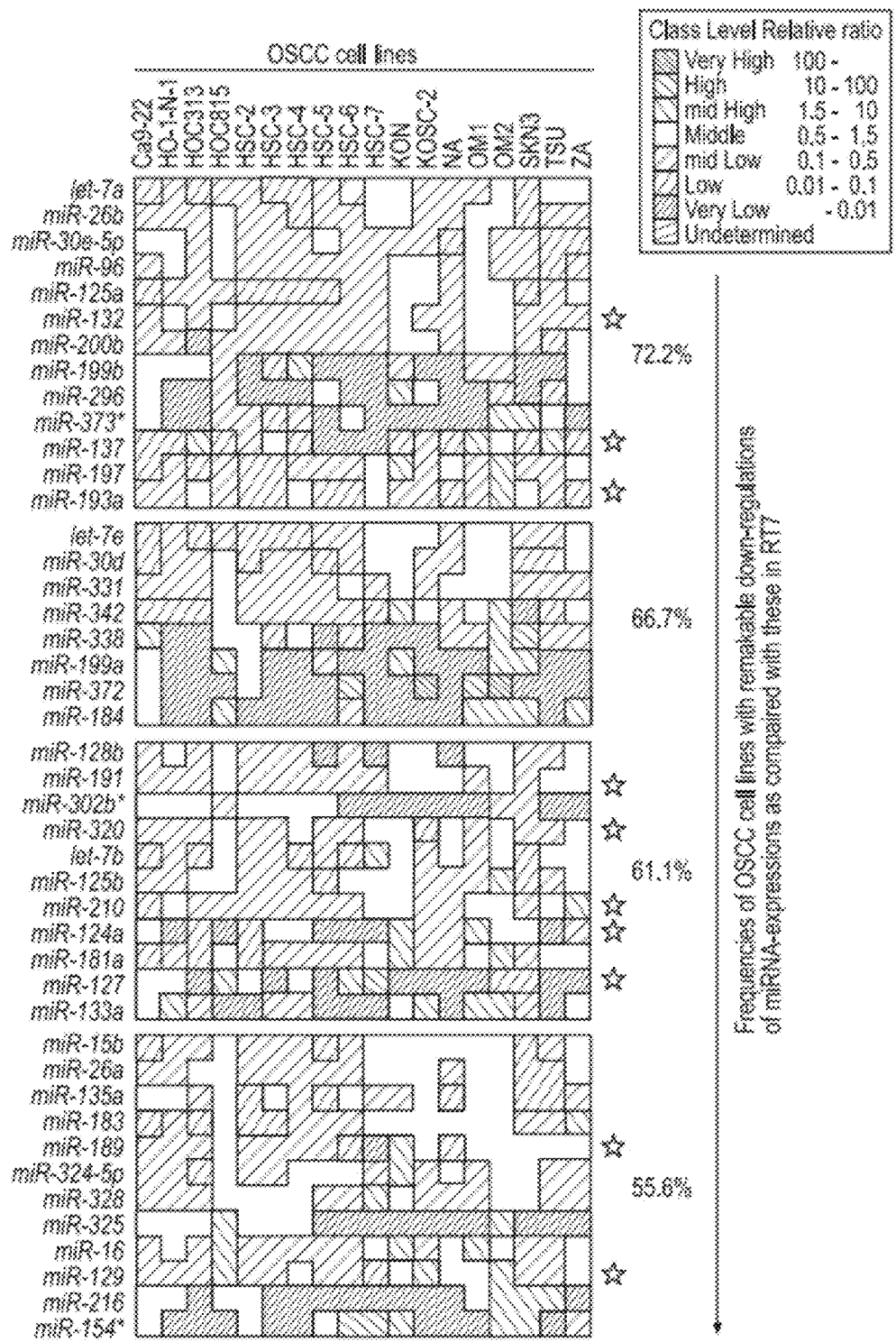
Figure 1B:
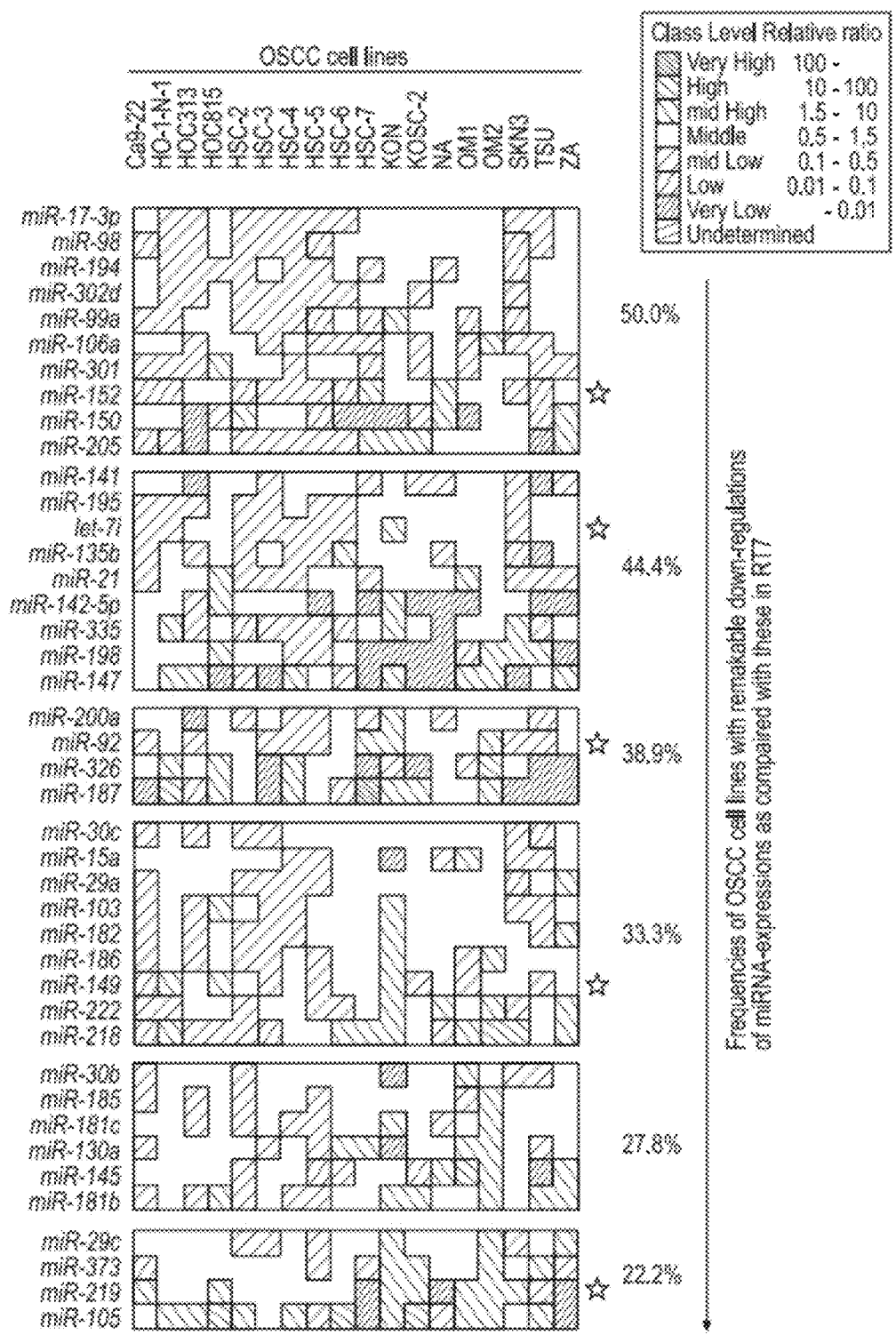
Figure 1B:
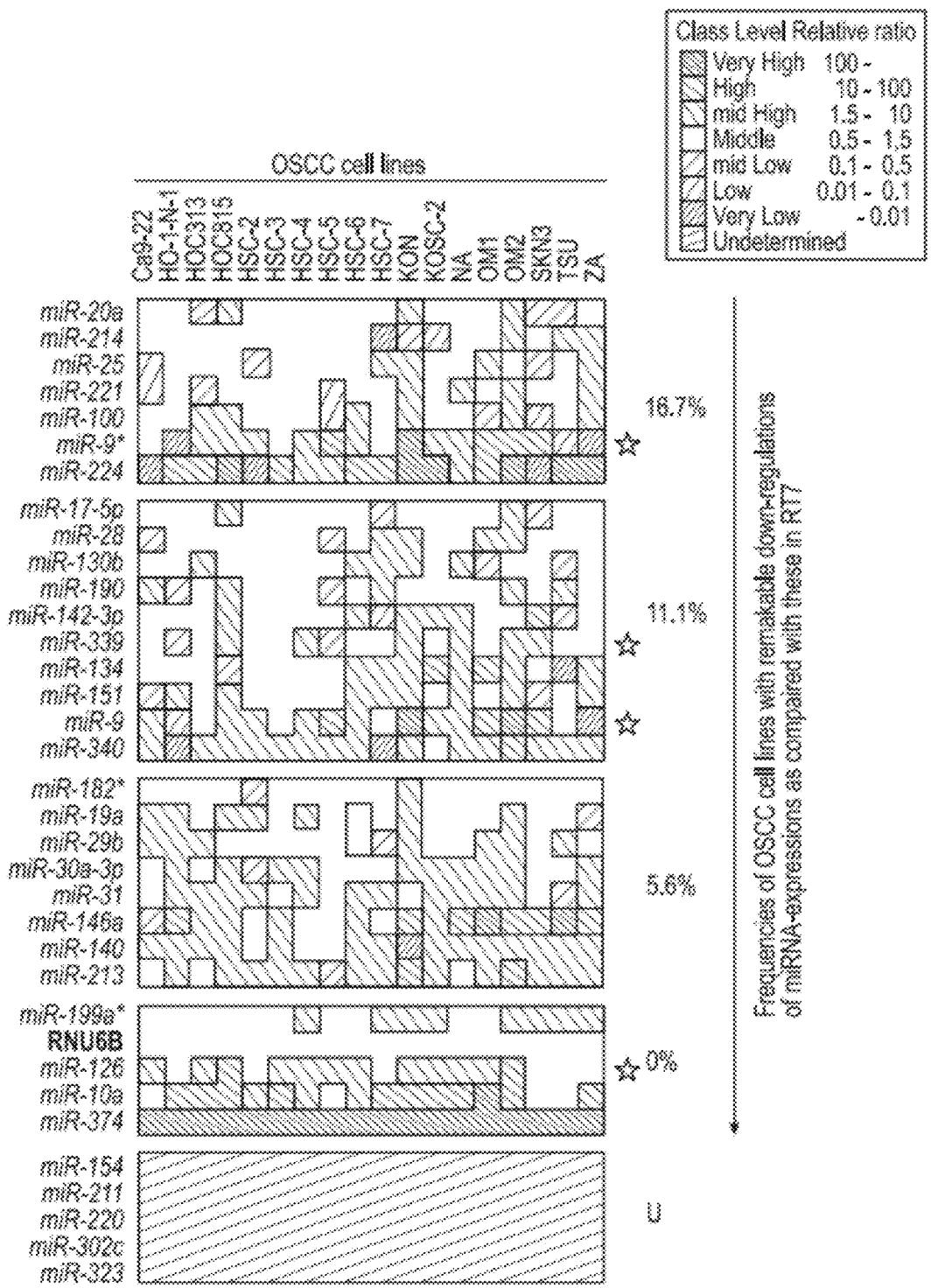
Figure 1C:
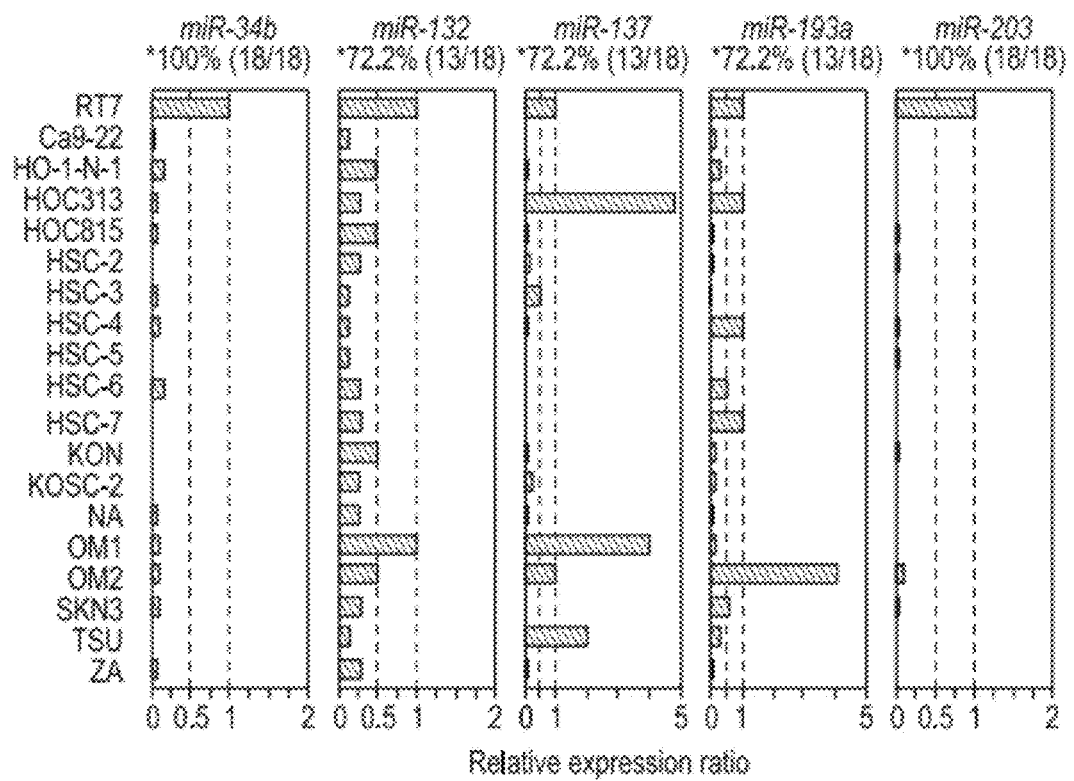

Among the 21 types of miRNA genes, the miR-34b, miR-132, miR-137, miR-193a, and miR-203 genes, the expression levels of which are down-regulated at high frequency in 18 types of oral squamous-cell carcinoma cells, had attracted attention. In comparison with the RT7 cells, the above five miRNA genes (i.e., miR-34b, miR-132, miR-137, miR-193a, and miR-203) exhibited significantly down-regulated expression levels in most oral squamous-cell carcinoma cell lines, and the percentages of such down-regulation were 100% (18/18), 72.2% (13/18), 72.2% (13/18), 72.2% (13/18), and 100% (18/18), respectively (FIGS. 1B and C).

Figure 1D:
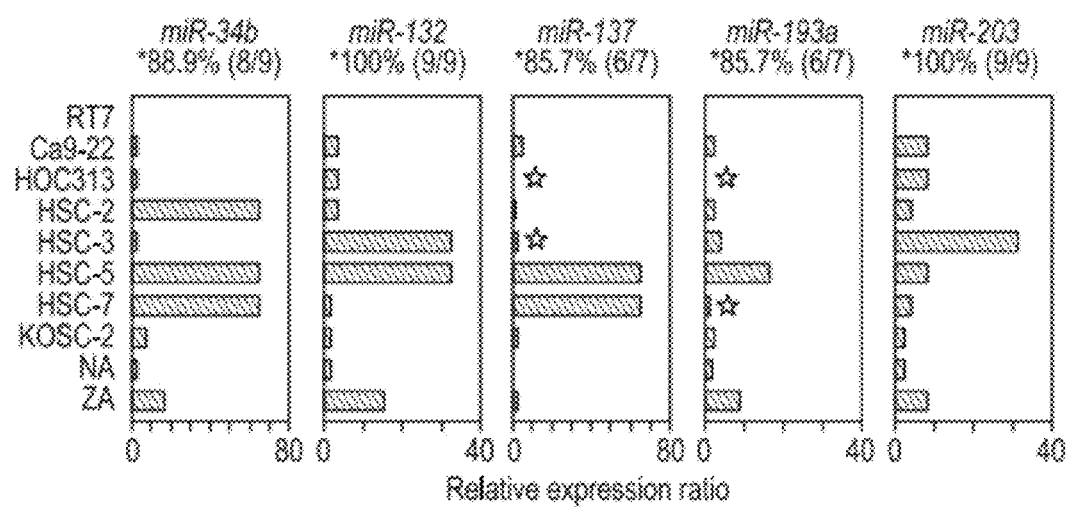

In order to inspect whether or not expression of these 5 types of miRNA genes was suppressed by DNA methylation, oral squamous-cell carcinoma cell lines in which these 5 types of miRNA genes had not been expressed were treated with 1 μM and 10 μM demethylating reagents (5-aza-dCyd) for 5 days. RNA was extracted from these cell lines and expression of candidate miRNA genes was inspected via real-time RT-PCR (FIG. 1D). As a result, expression of these genes was found to be recovered via treatment with 5-aza-dCyd. These results apparently suggest that DNA methylation is associated with expression suppression of these miRNA genes.

Figure 2A:
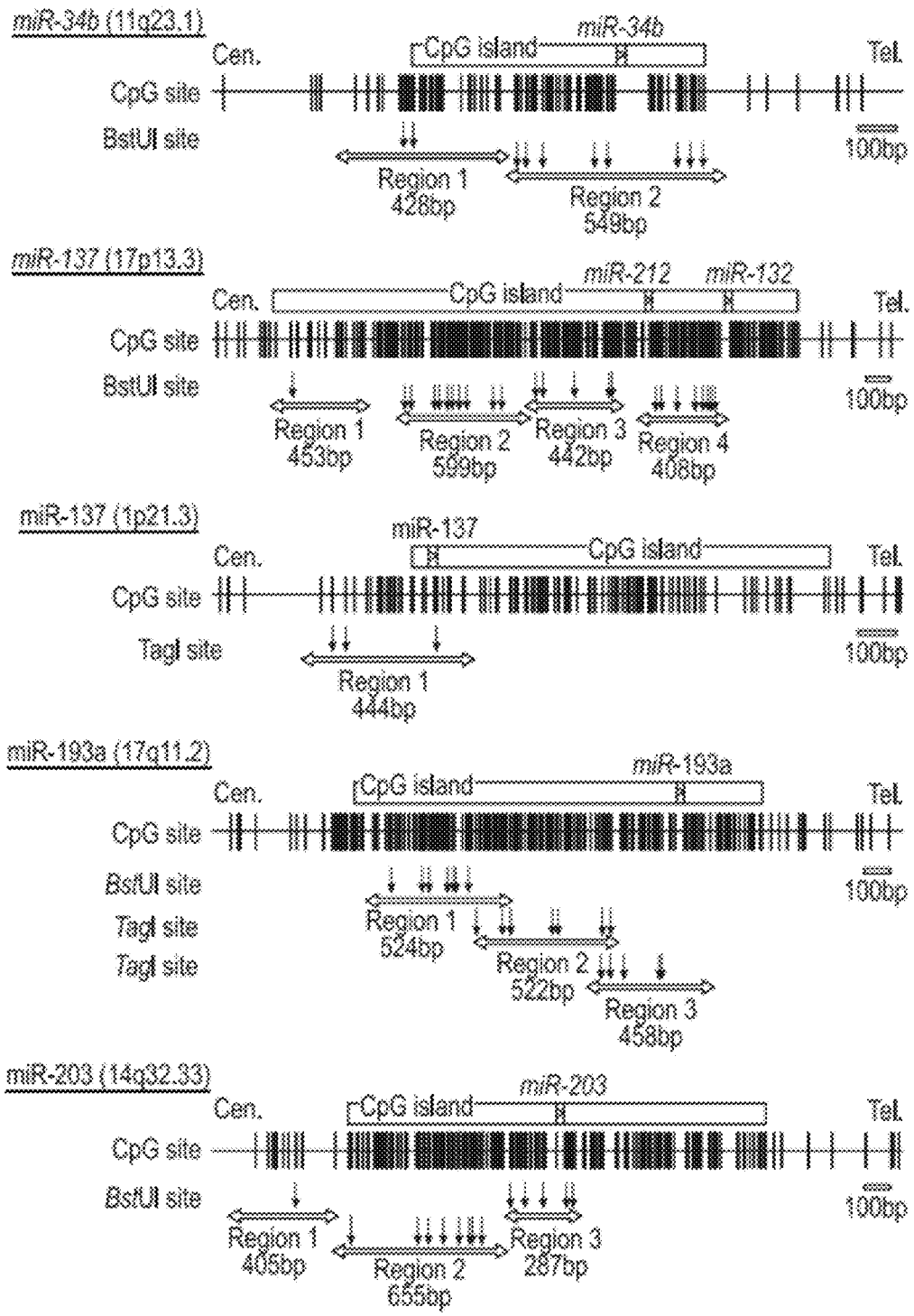
FIG. 2 shows the correlation analysis of the extent of methylation and expression of five types of candidate miRNA in the oral squamous-cell carcinoma cells. FIG. A is a map showing the physical relationship of miRNA, CpG islands, the CpG sites, and PCR products used for the COBRA method and the bisulfite sequencing in the genome. A dark gray box represents CpG islands; a light gray box represents an miRNA gene, a vertical line represents a CpG site, a horizontal arrow represents a PCR product, and a vertical arrow represents a restriction enzyme site. The size of the PCR product in the miR-34b region 1 was 428 by (cleaved with BstUI), that in the miR-34b region 2 was 549 by (cleaved with BstUI); that in the miR-132 region 1 was 453 by (cleaved with BstUI), that in the miR-132 region 2 was 599 by (cleaved with BstUI), that in the miR-132 region 3 was 442 by (cleaved with BstUI), that in the miR-132 region 4 was 408 by (cleaved with BstUI); that in the miR-137 region 1 was 444 by (cleaved with TaqI); that in the miR-193a region 1 was 524 by (cleaved with BstUI), that in the miR-193a region 2 was 522 by (cleaved with TaqI), that in the miR-193a region 3 was 458 by (cleaved with TaqI); that in the miR-203 region 1 was 405 by (cleaved with BstUI), that in the miR-203 region 2 was 655 by (cleaved with BstUI), and that in the miR-203 region 3 was 287 by (cleaved with BstUI). FIG. B shows the results of COBRA of the oral squamous-cell carcinoma cell lines and the RT7 cells. Expression patterns of candidate miRNA in 18 types of oral squamous-cell carcinoma cell lines are shown above the results of COBRA. An arrow represents a nonmethylated allele, an arrowhead represents a methylated allele, a star represents a sample in which a restriction enzyme fragment derived from a methylated allele has been detected, and asterisks (*) represent frequency of oral squamous-cell carcinoma cell lines in which the extent of DNA methylation of candidate miRNA was in accord with down-regulation of expression levels. FIG. C shows the results of bisulfite sequencing for the RT7 cells, the candidate miRNA expression-positive cell lines (+), and the candidate miRNA expression-negative cell lines (−). A map showing the physical relationship of miRNA, CpG islands, the CpG sites, and PCR products used for the COBRA method and the bisulfite sequencing in the genome is shown above the results of bisulfite sequencing. A light gray box represents an miRNA gene, a vertical line represents a CpG site, a horizontal arrow represents a PCR product, and a vertical arrow represents a restriction enzyme site. White and black squares each show nonmethylated and methylated CpG sites, and a lane is derived from a single type of clone.

In order to determine whether or not the state of DNA methylation of the 5 types of miRNA genes is correlated with the gene expression patterns in 18 types of oral squamous-cell carcinoma cell lines and in the RT7 cell line, the states of DNA methylation of the genes were analyzed by using the combined bisulfite restriction analysis (COBRA) method. FIG. 2A shows the correlation of CpG islands in the 5 types of miRNA genes and the primer positions used for the COBRA method.

Specifically, the EZ DNA methylation kit (Zymo Research, California, U.S.A.) was used to treat 2 μg of genomic DNA derived from the oral squamous-cell carcinoma cell lines in sodium bisulfite at 50° C. overnight, and PCR was carried out using the primers designed so as to amplify the target regions (Table 4) (SEQ ID NOs: 1 to 26 of the Sequence Listing).

TABLE 4

Primers for COBRA and bisulfite sequencing

| Seq ID No | miRNA | Region | | Primer from 5' to 3' | Product size |
|---|---|---|---|---|---|
| 1 | miR-34b | 1 | Forward | GGAGTGGAGGAGTTTTTTGTT | 428 bp |
| 2 | | | Reverse | AAATACCAAACCTCCCCTTC | |
| 3 | | 2 | Forward | TTAGTTTTAGGGTTTGGGGTT | 698 bp |
| 4 | | | Reverse | TTATAACCACCACAATACAATCAA | |
| 5 | miR-132 | 1 | Forward | TTTTGGTTTTAGATTGTTTATTG | 453 bp |
| 6 | | | Reverse | AAACTATTACCTCCAATTCCC | |
| 7 | | 2 | Forward | GTTTYGGAAAGTTAATTTTTTG* | 599 bp |
| 8 | | | Reverse | CCTCACTTTCCTAAAAAAATAAC | |
| 9 | | 3 | Forward | GTTATTTTTTTAGGAAAGTGAGG | 442 bp |
| 10 | | | Reverse | ACTCTACTACTCCRCCTCC** | |

TABLE 4-continued

Primers for COBRA and bisulfite sequencing

| Seq ID No | miRNA | Region | Primer | from 5' to 3' | Product size |
|---|---|---|---|---|---|
| 11 | | 4 | Forward | TTTTGGTTTTAGATTGTTTATTG | 408 bp |
| 12 | | | Reverse | AAACTATTACCTCCAATTCCC | |
| 13 | miR-137 | 1 | Forward | TTTTTTTGTGTTAAGTATTTGATTT | 444 bp |
| 14 | | | Reverse | AAAAAAATACTACCTTAACAACCA | |
| 15 | miR-193a | 1 | Forward | AAAGGGAAAATTATTGGGTTT | 524 bp |
| 16 | | | Reverse | AACCCCTCRAACTCCTAA** | |
| 17 | | 2 | Forward | TTTTAATTTTYGAGGGGTT* | 522 bp |
| 18 | | | Reverse | CAACCCTCCAAAAATTACA | |
| 19 | | 3 | Forward | GAGGTTTTGGTTTTYGTATTT* | 458 bp |
| 20 | | | Reverse | CCTTCTCCAACRTAAACCT** | |
| 21 | miR-203 | 1 | Forward | TTAGATTTGGGGTAAGTGTTGA | 405 bp |
| 22 | | | Reverse | CCCTCTCACTTCAAAAAAACT | |
| 23 | | 2 | Forward | AGTTTTTTTTGAAGTGAGAGGG | 655 bp |
| 24 | | | Reverse | CACCCCCTACCCTACTACAA | |
| 25 | | 3 | Forward | GTTGTAGTAGGGTAGGGGGT | 287 bp |
| 26 | | | Reverse | ACCCCTAACTATAACTCTAACTCCA | |

*Two kinds of forward primers, which changed a part of "Y" into "C" or "T", were mixed and used to amplify the bisulfite-modified genomic DNA.
**Two kinds of reverse primers, which changed a part of "R" into "G" or "A", were mixed and used to amplify the bisulfite-modified genomic DNA.

Figure 2B:
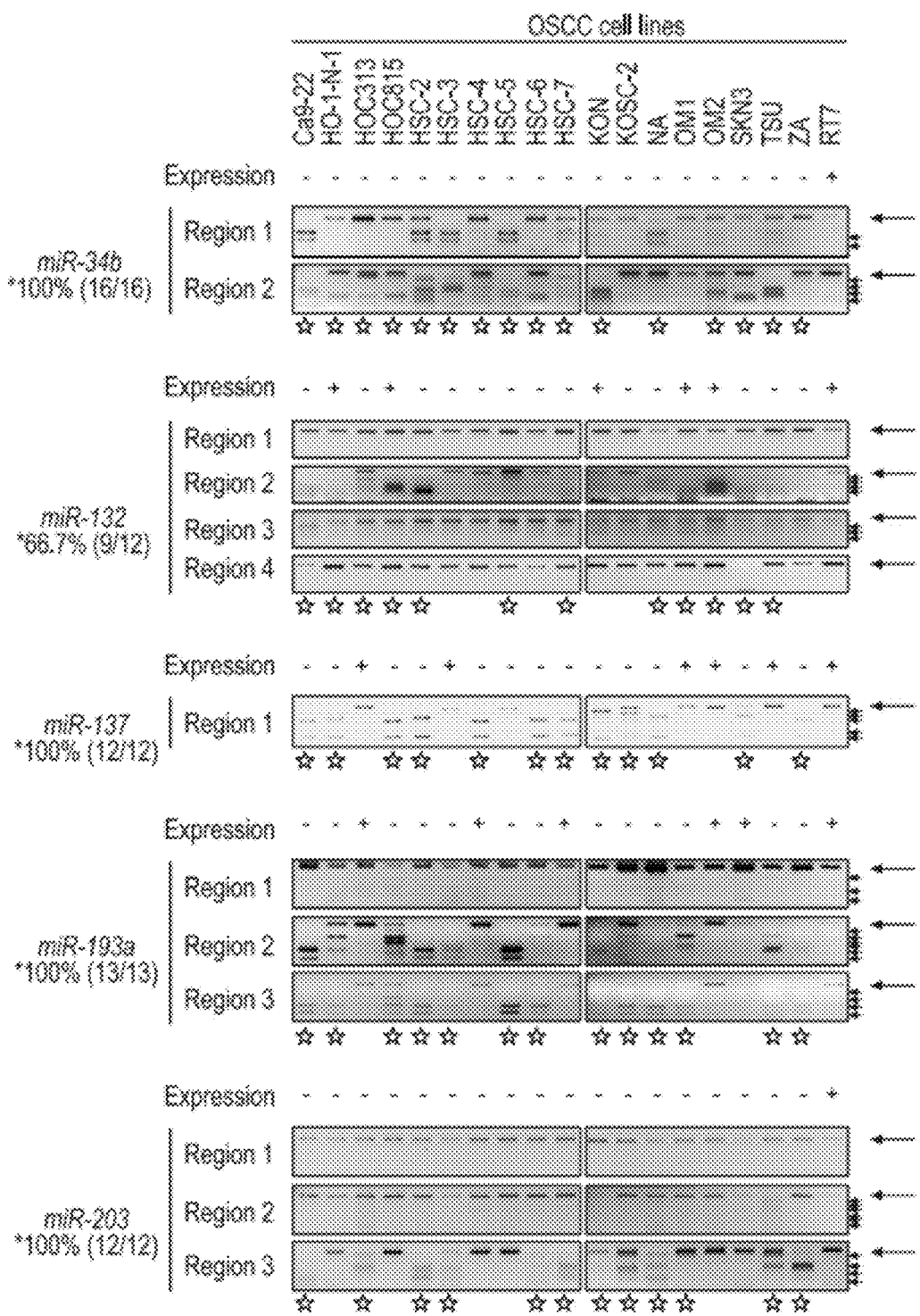
Figure 2C:
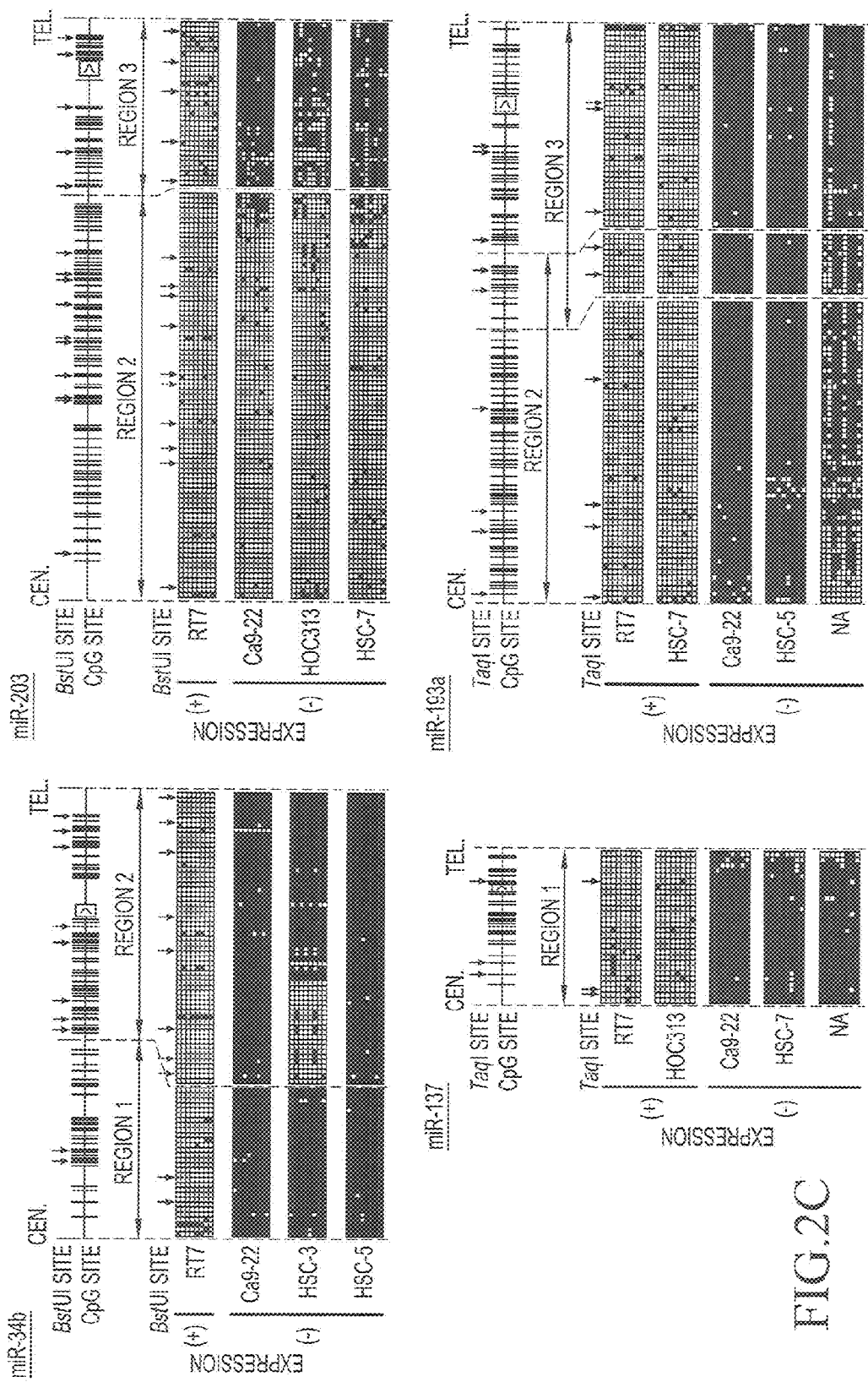

The resulting PCR products were digested with the BstUI restriction enzyme (New England BioLabs) or the TaqI restriction enzyme (New England BioLabs). BstUI or TaqI does not digest unmethylated sequences modified with sodium bisulfite, but digests methylated sequences that are not modified with sodium bisulfite. By utilizing these properties, after PCR fragment was subjected to electrophoresis, the density of the band of the methylated fragment and that of the unmethylated fragment were assayed by densimetry using the MultiGauge 2.0 (Fuji Film), and the extent of methylation of the methylated region was represented in terms of percentage. These sequences were subcloned into a TOPO TA cloning vector (Invitrogen), and the nucleotide sequences were determined As a result, in the vicinities of the miR-34b, miR-137, miR-193a, and miR-203 genes, other than the miR-132 gene, hypermethylation of CpG islands or in the vicinity thereof was observed in all the oral squamous-cell carcinoma cell lines in which down-regulation or quenching of gene expression has been confirmed (FIG. 2B). In accord with the results of the COBRA method, hypermethylation in the oral squamous-cell carcinoma cell lines in which down-regulation or quenching of four types of miRNA gene expression levels had been confirmed, were verified via bisulfite sequencing (FIG. 2C).

In order to thoroughly analyze miRNA gene expression and DNA methylation in specimens obtained from patients with oral squamous-cell carcinoma based on the above results, 4 types of genes (miR-34b, miR-137, miR-193a, and miR-203) were selected.

Example 3

Analysis of miRNA Expression and Methylation in Specimen from Patient with Oral Squamous-Cell Carcinoma Whether or not methylation of four types of miRNA genes has occurred in cancerous tissue of a patient with oral squamous-cell carcinoma and the correlation between the state of DNA methylation of the four types of miRNA genes and the expression patterns in cancerous tissue of a patient with oral squamous-cell carcinoma were analyzed by using the COBRA method and TaqMan real-time RT-PCR analysis.

Regarding cancerous and noncancerous tissue samples of patients with oral squamous-cell carcinoma, 11 cases of frozen samples (T1: 0 cases; T2: 10 cases; T3: 0 cases; T4: 1 case) were obtained with the approval of the Ethics Committee of Tokyo Dental and Medical University, followed by acquisition of written agreements from patients with oral squamous-cell carcinoma who had undergone surgery at the Tokyo Dental and Medical University Hospital, Faculty of Dentistry. The relevant stage was determined in accordance with TNM classification of the Union International Contre le Cancer (UICC).

Figure 3A:
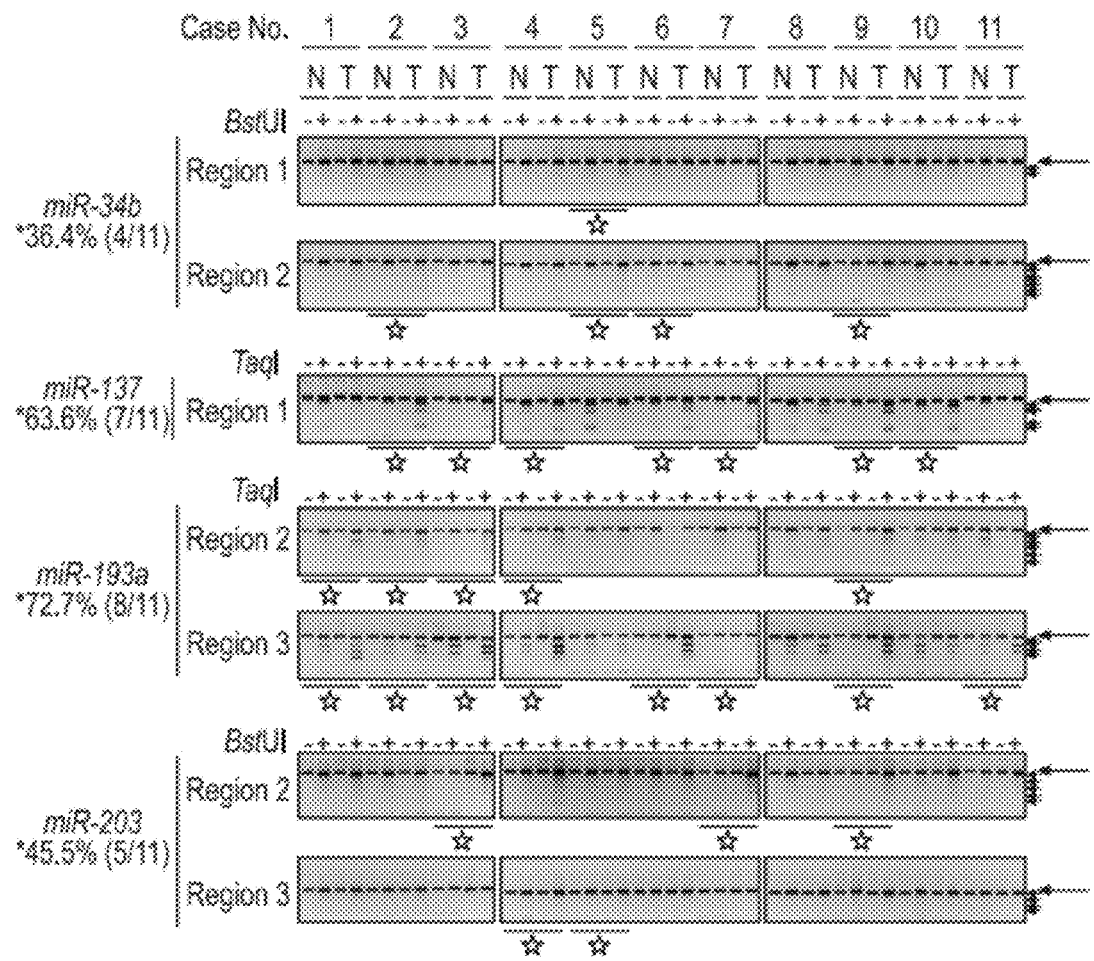
FIG. 3 shows the methylation analysis and the expression analysis of cancerous and non-cancerous tissue for 11 cases of patients with oral squamous-cell carcinoma. FIG. A shows the results of COBRA for the candidate miRNA gene of cancerous sites (T) of surgically removed oral squamous-cell carcinoma from 11 patients and for corresponding noncancerous tissue (N). Whether or not the cells have been treated with a restriction enzyme is indicated by the symbol "+" or "−" above the results of COBRA. A star represents a case in which cancer-specific hypermethylation has been detected. Asterisks (*) represent frequency of cancer-specific hypermethylation of candidate miRNA determined via COBRA. FIG. B shows the results of quantitative real-time RT-PCR analysis of candidate miRNA expression in cancerous sites and in noncancerous tissue obtained from 11 patients with oral squamous-cell carcinoma. A star represents a case in which cancer-specific hypermethylation has been detected. Asterisks (*) represent frequency of cases in which cancer-specific hypermethylation has been detected via COBRA and candidate miRNA expression is down-regulated in cancerous tissue (expression levels of less than 0.5-fold), compared with noncancerous tissue. FIG. C shows representative examples of the results of bisulfite sequencing. A horizontal arrow represents a PCR product, a vertical arrow represents a restriction enzyme site, white and black squares each show nonmethylated and methylated CpG sites, and a lane is derived from a single type of clone.

The COBRA method revealed that hypermethylation of cancer-specific DNA of miR-34b, miR-137, miR-193a, and miR-203 was observed in the cancerous tissue of patients with oral squamous-cell carcinoma at frequencies of 36.4% (4/11), 63.6% (7/11), 72.7% (8/11), and 45.5% (5/11), respectively (FIG. 3A). In the carcinoma-specific hypermethylation-positive cases of miR-137 and miR-193a, apparent fragments derived from alleles that had been methylated in a carcinoma-specific manner were observed.

In many of the carcinoma-specific hypermethylation-positive cases of miR-34b and miR-203, the amount of fragments derived from methylated alleles was very small. This result indicates that the frequency of carcinoma-specific hypermethylation in the vicinity of miR-34b or miR-203 is very low in cancer cells.

Figure 3B:
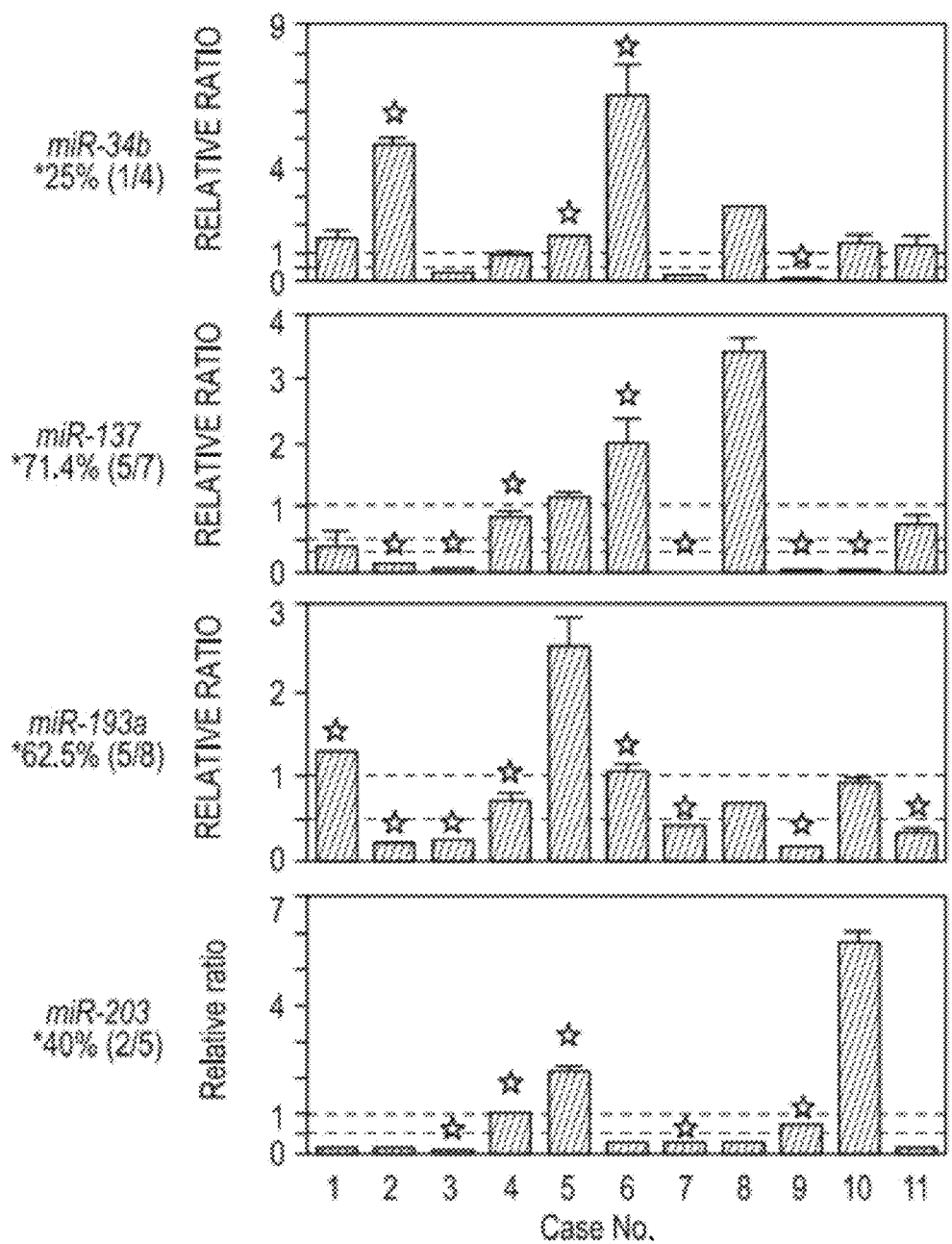
Figure 3C:
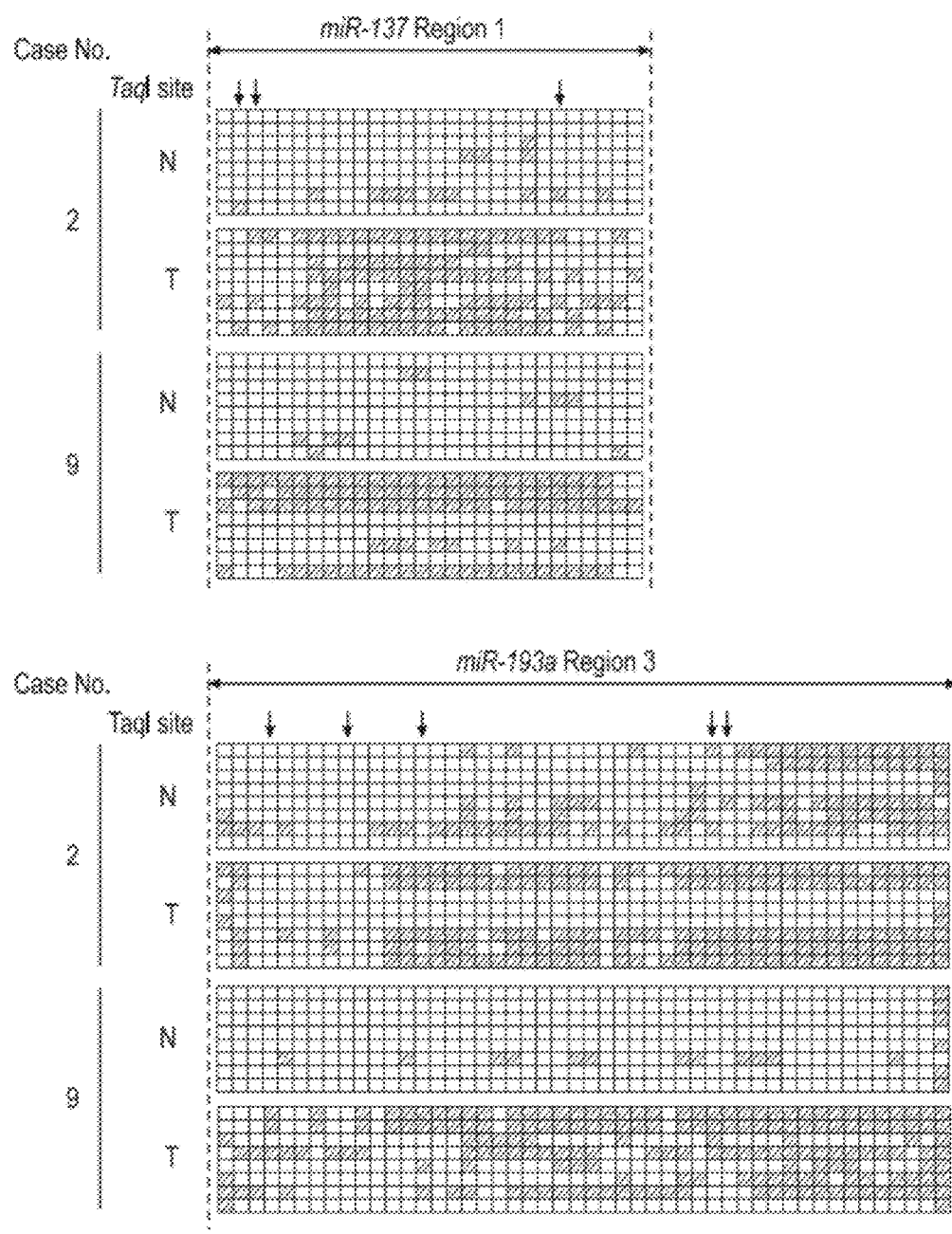

When the normal oral cavity mucosa was compared with a cancerous site via TaqMan real-time RT-PCR analysis, expression levels of miR-34b, miR-137, miR-193a, and miR-203 were significantly down-regulated (i.e., 27.2% (3/11), 54.5% (6/11), 45.5% (5/11), and 72.7% (8/11) of oral squamous-cell carcinoma cases) (FIG. 3B). The percentages of oral squamous-cell carcinoma cases in which both carcinoma-specific DNA hypermethylation and down-regulated or quenched expression of miR-34b, miR-137, miR-193a, and miR-203 were observed were 25% (1/4), 71.4% (5/7), 62.5% (5/8), and 40% (2/5), respectively. This strongly suggests that expression of miR-137 and miR-193a is suppressed via carcinoma-specific hypermethylation in oral squamous-cell carcinoma. Also, bisulfate sequencing of such miRNA in the oral squamous-cell carcinoma cases apparently verifies the results of the COBRA method (FIG. 3C).

Example 4

Effects of miR-137 and miR-193a for Suppressing Carcinoma in the Growth of Oral Squamous-Cell Carcinoma Cell Line Synthetic double-stranded RNA (dsRNA) comprising miR-137 and miR-193a sequences were transiently introduced into the oral squamous-cell carcinoma cell lines in which down-regulated or quenched expression of miR-137 and miR-193a has been observed. Thus, the effects of miR-137 and miR-193a for suppressing cell growth were examined.

Specifically, synthetic double-stranded RNA comprising miR-137 and miR-193a sequences (i.e., the Pre-miR™ miRNA Precursor Molecule (10 nM, Ambion)) or non-specific miRNA as a control (i.e., PremiR™ Negative Control#1 (Ambion)) was transfected into oral squamous-cell carcinoma cell lines using Lipofectamine RNAiMAX (Invitrogen) in accordance with the manufacturer's instructions. The viable cell counts 24 to 72 hours after the transfection were evaluated via WST assay. The results were normalized with the use of the counts of control cells into which nonspecific miRNA had been introduced.

Figure 4A:
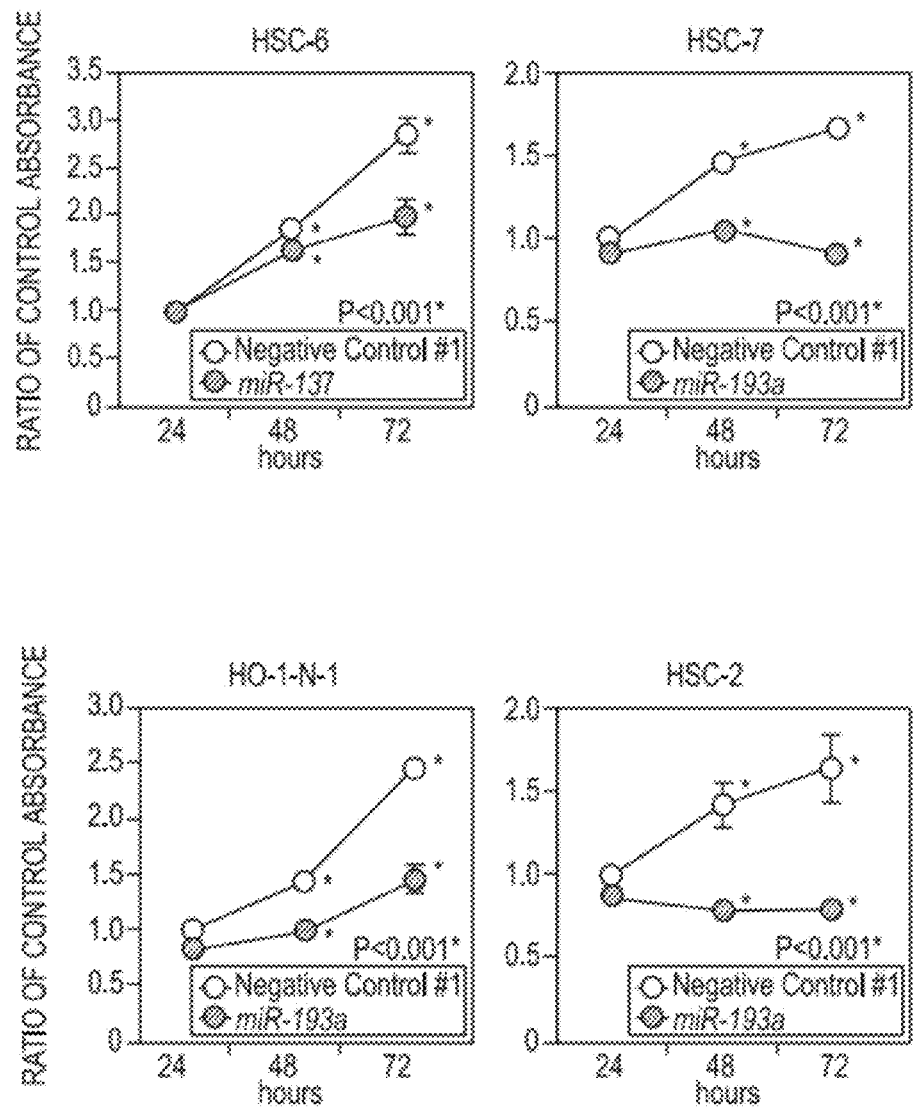
FIG. 4 shows the effects of miR-137 and miR-193a for suppressing carcinoma in the oral squamous-cell carcinoma cell lines. FIG. A shows the growth curve and the phase contrast microscopic photograph of oral squamous-cell carcinoma cell lines after the transfection of 10 nM of Pre-miR™ miRNA Precursor Molecule or nonspecific miRNA as a control using Lipofectamine RNAiMAX. The viable cell counts 24 to 72 hours after the transfection were evaluated by WST assay. The results of the experiments are shown in terms of the average (bar, SE) of three assay operations at each data point. The phase contrast microscopic photograph shows the cells that have been cultured for 72 hours after the transfection. FIG. B shows a TUNEL stain image of HSC-2 cells 24 hours after the transfection of miR-193a or nonspecific dsRNA as a control under a fluorescent microscope. FIG. C shows apoptosis induction in HSC-2 cells 24 hours after the transfection of miR-193a or nonspecific dsRNA as a control.
Figure 4B:
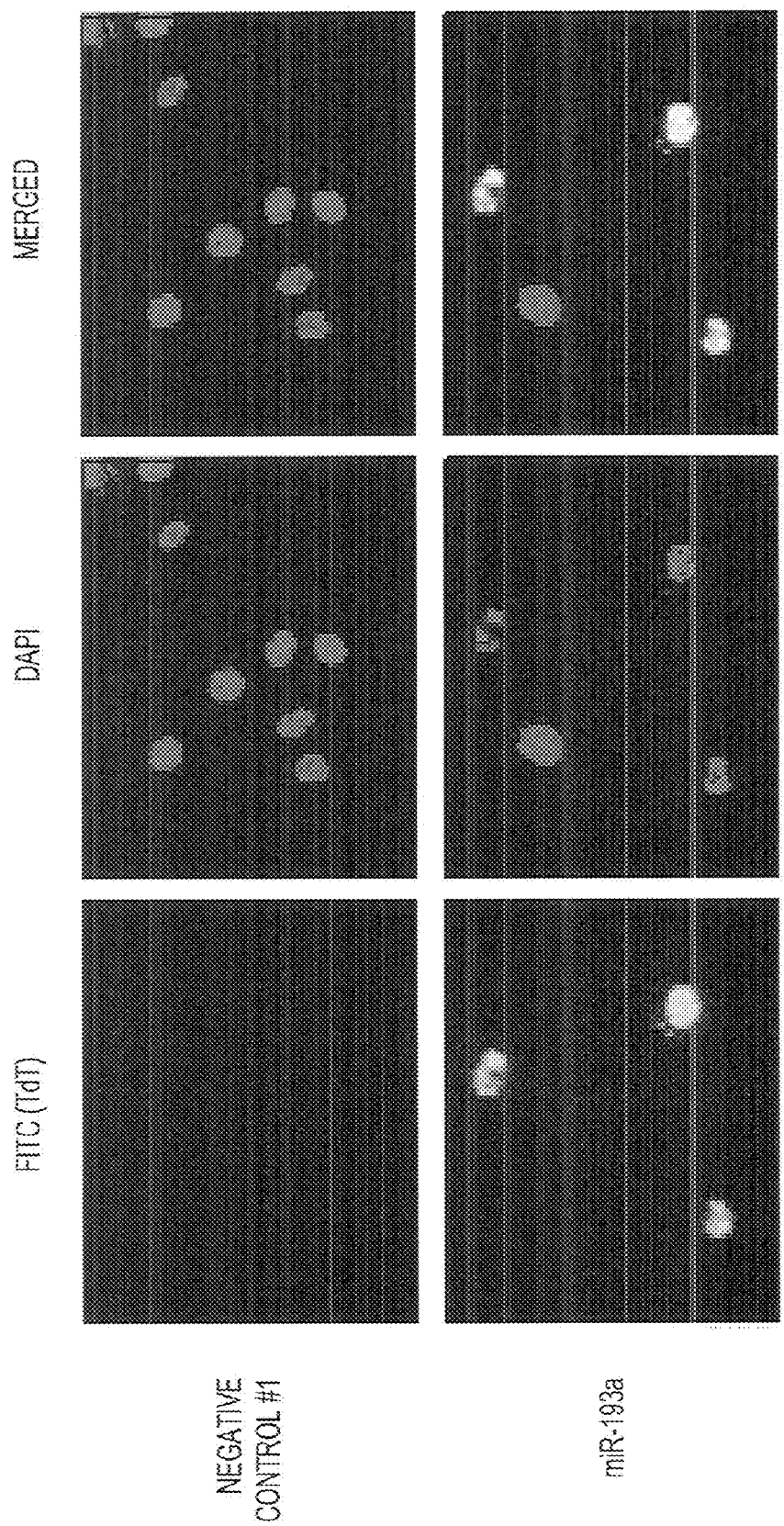
Figure 4C:
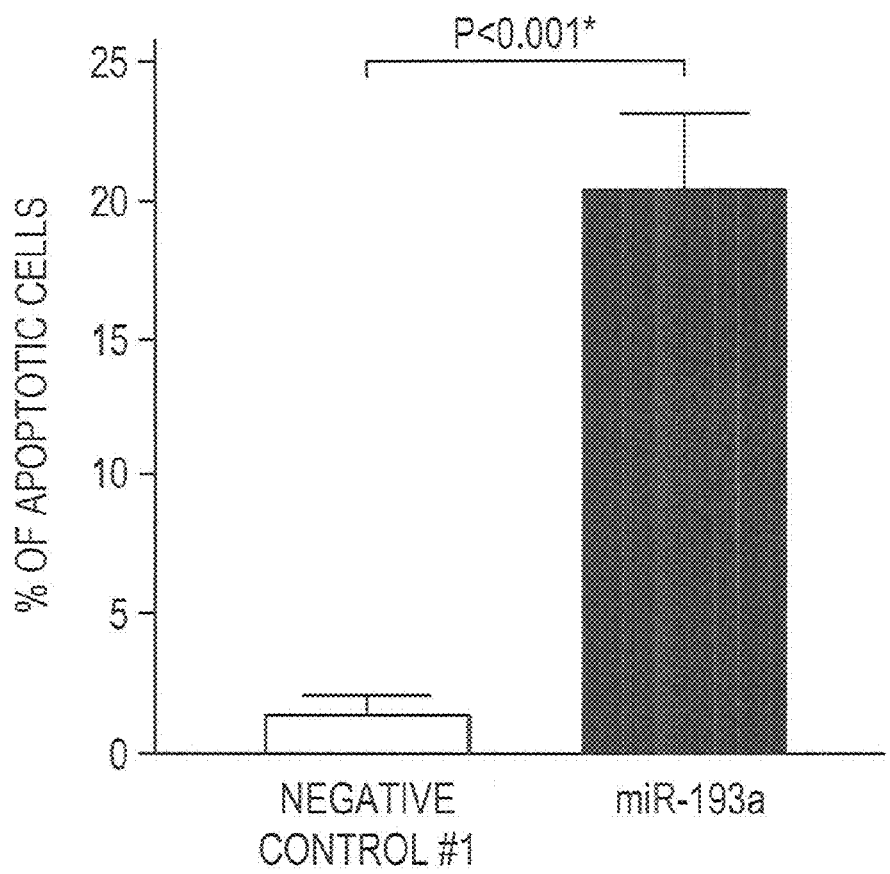

The above analysis revealed that introduction of miR-137 and miR-193a genes resulted in significant suppression of growth of oral squamous-cell carcinoma cells (FIG. 4A). This suggests that miR-137 and miR-193a have functions of suppressing carcinoma. Also, the TUNEL analysis revealed that lowered capacity for cell growth resulting from miR-193a gene introduction was caused by apoptosis (FIG. 4B). The TUNEL analysis was carried out using a TUNEL staining Kit (MEBSTAIN Apoptosis Kit Direct; MBL), which can enzymatically label and detect cleavage of DNA strands in the cells 24 hours after the transfection, in accordance with the manufacturer's instructions.

The invention claimed is:

1. A method for suppressing growth of oral squamous-cell carcinoma cells, wherein the method comprises introducing at least one gene selected from the group consisting of miR-137 and miR-193a into the oral squamous-cell carcinoma cells.

2. The method according to claim 1, wherein the gene is bound to or incorporated in a polymer compound.

3. The method according to claim 2, wherein the polymer compound is a liposome.

* * * * *